US009279770B2

(12) United States Patent
Mossoba et al.

(10) Patent No.: US 9,279,770 B2
(45) Date of Patent: Mar. 8, 2016

(54) MID-INFRARED IMAGING OF MICROARRAYS

(75) Inventors: Magdi M. Mossoba, Great Falls, VA (US); Sufian Al-Khaldi, Bowie, MD (US); Brianna Schoen, Abingdon, VA (US); Betsy Jean Yakes, Alexandria, VA (US)

(73) Assignee: THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 13/879,157

(22) PCT Filed: Oct. 14, 2011

(86) PCT No.: PCT/US2011/056248
§ 371 (c)(1),
(2), (4) Date: May 21, 2013

(87) PCT Pub. No.: WO2012/051476
PCT Pub. Date: Apr. 19, 2012

(65) Prior Publication Data
US 2014/0148352 A1 May 29, 2014

Related U.S. Application Data

(60) Provisional application No. 61/393,635, filed on Oct. 15, 2010.

(51) Int. Cl.
*C12Q 1/68* (2006.01)
*C12M 1/34* (2006.01)
*C07H 21/02* (2006.01)
*C07H 21/04* (2006.01)
*G01J 5/00* (2006.01)
*G01J 3/00* (2006.01)
*C40B 30/04* (2006.01)
*G01N 21/75* (2006.01)

(52) U.S. Cl.
CPC .............. *G01N 21/75* (2013.01); *C12Q 1/6816* (2013.01); *C12Q 1/6837* (2013.01)

(58) Field of Classification Search
CPC ...... C12Q 1/68; C12Q 1/6816; C12Q 1/6837; G01N 21/75; C40B 30/04; G01J 5/00
USPC ............. 435/6.1, 6.11, 287.2; 536/23.1, 24.3; 977/773; 250/338.1; 356/51; 506/9
See application file for complete search history.

(56) References Cited

U.S. PATENT DOCUMENTS

| 5,445,934 A | 8/1995 | Fodor et al. |
| 5,653,939 A | 8/1997 | Hollis et al. |
| 5,774,305 A | 6/1998 | Boutaghou |
| 6,092,302 A | 7/2000 | Berrigan |
| 6,133,043 A | 10/2000 | Talley et al. |
| 6,376,177 B1 | 4/2002 | Poponin |
| 6,396,995 B1 | 5/2002 | Stuelpnagel et al. |
| 6,544,732 B1 | 4/2003 | Chee et al. |
| 6,897,965 B2 * | 5/2005 | Ghadiri .................. G01N 21/45 356/519 |
| 7,015,471 B2 * | 3/2006 | Franzen ........... G01N 33/54373 250/338.1 |
| 7,255,835 B2 * | 8/2007 | Franzen ............... G01N 21/552 250/339.07 |
| 7,642,344 B2 | 1/2010 | Van Ness et al. |
| 2004/0180369 A1 | 9/2004 | Franzen et al. |

FOREIGN PATENT DOCUMENTS

| JP | 2006105879 A | 4/2006 |
| JP | 3955952 B2 | 5/2007 |
| WO | 0072018 A1 | 11/2000 |
| WO | WO0072018 | * 11/2000 |

OTHER PUBLICATIONS

Yamaguchi et al. Journal of applied physics 102.1 (2007): 014303; 7 pages.*
Chan et al. Analyst 131.1 (2006): 126-131.*
Kong et al. Appl Microbiol Biotechnol (2007) 77:223-232.*
Sonnleitner et al. Biomedical Optics 2005. International Society for Optics and Photonics, 2005; pp. 202-210.*
Shalon et al. Genome Res. 1996 6: 639-645.*
Brewer et al.; "Detection of DNA Hybridization on Gold Surfaces by Polarization Modulation Infrared Reflection Absorption Spectroscopy"; Langmuir; 18; pp. 44600-4464; (2002).
Chan et al.; "Detection of Trace Materials with Fourier Transform Infrared Spectroscopy Using a Multi-Channel Detector"; Analyst; 131; pp. 126-131; (2006).
Ishibashi et al.; "In situ Study of DNA Attachment and Hybridization at Silicon Survaces by Infarared Absorption Spectroscopy"; Japanese Journal of Applied Physics; 47(4); pp. 3204-3208; (2008).
International Search Report and Written Opinion; International Filing Date Oct. 14, 2011; Date of Mailing Jan. 17, 2012; Applicant's File Reference NIH0053PCT (NIH0053US2); 15 pages.
Kelly et al.; "Discrimination of Base Differences in Oligonucleotides Using Mid-Infrared Spectroscopy and Multivariate Analysis"; Anl. Chem.; 81; pp. 5314-5319; (2009).
Kopf et al.; "Detectioin of Hybridization on Nanografted Oligonucleotides Using Scanning Near-Field Infrared Microscopy"; J. Phys. Chem.; 114; pp. 1306-1311; (2010).
Li et al.; "DNA Microarrays: Their Use and Misuse"; Microcirculation; 9; pp. 13-22; (2002).
Li et al., "Single-Nucleotide Polymorphism Genotyping by Nanoparticle-Enhanced Surface Plasmon Resonance Imaging Measurements of Surface Ligation Reactions"; Anal. Chem.; 78; pp. 3158-3164; (2006).

(Continued)

*Primary Examiner* — Narayan Bhat
(74) *Attorney, Agent, or Firm* — Cantor Colburn LLP

(57) ABSTRACT

Described herein are methods for mid-infrared imaging of nucleic acid microarrays by employing mid-infrared reflective labels combined with detection in the reflection mode. The methods described herein provide intrinsic image contrast, and permit detection of DNA microarray hybridization on infrared absorbing substrates such as glass slides.

16 Claims, 11 Drawing Sheets

(56) References Cited

OTHER PUBLICATIONS

Liao et al.; FTIR-ATR Detection of Proteins and Small Molecules Through DNA Conjugation; Sensors and Actuators B 114; pp. 445-450; (2006).

Moses et al.; "Characterization of Single- and Double-Stranded DNA on Gold Surfaces"; Langmuir; 20; pp. 11134-11140; (2004).

Mossoba et al.; "Nanoparticle Probes and Mid-Infrared Chemical Imaging for DNA Microarray Detection"; Applied Spectroscopy; 64(11); pp. 1191-1198; (2010).

Shalon et al.; "A DNA Microarray System for Analyzing Complex DNA Samples Using Two-color Fluorescent Probe Hybridization"; Genome Research; 6(7); pp. 639-645; (1996).

Taton et al.; "Scanometric DNA Array Detection with Nanoparticle Probes"; Science; 289; pp. 1757-1760; (2000).

Tokareva et al.; "Hybridization of Oligonucleotide-Modified Silver and Gold Nanoparticles in Aqueous Dispersions and on Gold Films"; Journal of the American Chemical Society; 126(48); pp. 15784-15789; (2004).

Waddell et al; "High-Resolution Near-Infrared Imaging of DNA Microarrays with Time-Resolved Acquisition of Fluorescence Lifetimes"; Anal Chem; 72(24), pp. 5907-5917; (2000).

Yamaguchi et al.; "Detection of DNA Molecules on Porous Si Surfaces by Infrared Spectromicroscopy"; Hyomen Kagaku; 26(9); pp. 537-541; (2005).

* cited by examiner

● – Control probes with the sequence of the forward PCR primer
○ – Microarray probes common for most *Mycoplasma species*
○ – Species-specific probes for identification of *Mycoplasma species*
◎ – Microarray probes common for most *Acholeplasma species*
◎ – Species-specific probes for identification of *Acholeplasma species*

FIG. 13
| 1 | 2 | 3 | 4 | 5 | 6 | 7 | 8 |
|---|---|---|---|---|---|---|---|
| QC | *virF* P1 | *virF* P2 | *virF* P5 | *ail* P3 | *ail* P4 | *ail* P5 | QC |
| QC | *yst* P8 | *yst* P4 | *yst* P5 | *blaA* P1 | *blaA* P3 | *blaA* P4 | QC |
| QC | 16S P1 | 16S P2 | 16S P3 | CPA | CPA | CPA | QC |
| QC | QC | QC | QC | QC | QC | QC | QC |
FIG. 14
*ail* P3, P4, P5 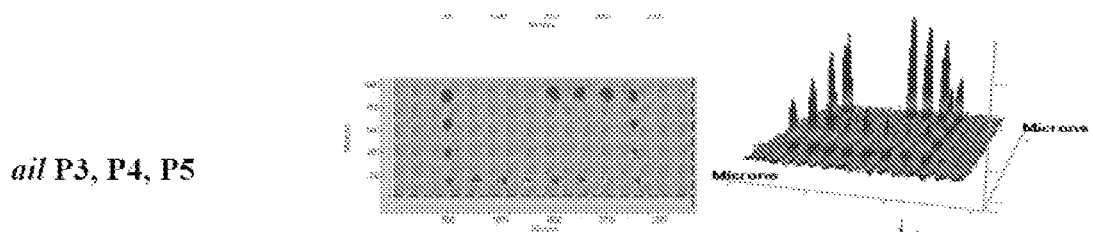
FIG. 15
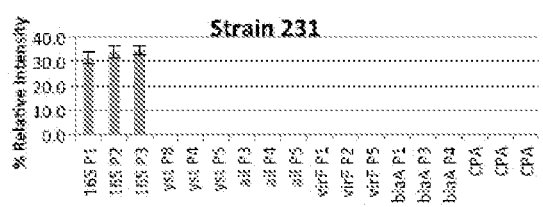

SEQUENCE LISTING

<160> NUMBER OF SEQ ID NOS: 32

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
acagacagat cattcaacct ct                                              22

<210> SEQ ID NO 2
<211> LENGTH: 22
<212> TYPE: DNA
<213> ORGANISM: Artificial Sequence
<220> FEATURE:

```
<223> OTHER INFORMATION: Primer

<400> SEQUENCE: 2
agttgaatta gatggagaac ca                                              22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggaaccctca gtagtttcaa gt                                              22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
agcatgagtc atagttggga tg                                              22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tgagtctcca gagaaatttg cg                                              22

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
ggtgaatacg ttctcgggtc ttgtacacac                                      30

<210> SEQ ID NO 7
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: n is a, c, g, or t

<400> SEQUENCE: 7
tncttttcac cttccctcac ggtac                                           25

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
```

```
gcttttgctt gcctttagct cg                                              22
```

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9

```
agaatacgtc gctcgcttat cc                                              22
```

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10

```
ttattcctct cggctctgcg                                                 20
```

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11

```
gcaaccgccc agaagaac                                                   18
```

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12

```
ggcatgggat taaccacatt ca                                              22
```

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13

```
tggttatgca caaagccatg t                                               21
```

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14

```
tggaagcggg ttgaattgca                                                 20
```

<210> SEQ ID NO 15
<211> LENGTH: 22
<212> TYPE: DNA

```
<213> ORGANISM: Artificial Sequence
<220> FEATURE:
<223> OTHER INFORMATION: Primer

<400> SEQUENCE: 15
acctgaagta ccgttatgaa ct                                              22

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gccatctttc cgcattaacg a                                               21

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
tcgtttgctt atacccatca gg                                              22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ttgaaataac taggctgggt cg                                              22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
gcaacataca tcacagcaat cc                                              22

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
aatagaatgc gtggtagacc g                                               21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
ctgttattga caccactgcg t                                               21
```

-continued

```
<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
tgagtgatgg aggatctatg aa                                              22

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
aaatgcgcta ccggcttcag                                                 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agtggtggta tcacgtgggt                                                 20

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
tgctgccacc attcaatata gt                                              22

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
aagccagtct cagccgaat                                                  19

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tcagatgttc agattagacc gc                                              22

<210> SEQ ID NO 28
<211> LENGTH: 20
<212> TYPE: DNA
<213> ORGANISM: Artificial Sequence
<220> FEATURE:
```

```
<223> OTHER INFORMATION: Primer

<400> SEQUENCE: 28
tctgggaaac tgcctgatgg                                              20

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ggtgcttctt ctgcgagtaa c                                            21

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
acactggaac tgagacacgg                                              20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cagcgaggag gaaggcataa                                              20

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ctagctggtc tgagaggatg a                                            21
```

MID-INFRARED IMAGING OF MICROARRAYS

CROSS-REFERENCE TO RELATED APPLICATIONS

The present application is a 371 of PCT/US2011/056248 filed on Oct. 14, 2011, which claims priority to U.S. Provisional Application Ser. No. 61/393,635 filed on Oct. 15, 2010, under the provisions of 35 U.S.C. 119 and the International Convention for the protection of Industrial Property, which are incorporated herein by reference in their entirety.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. The Government may have certain rights in this invention.

BACKGROUND

This disclosure relates to methods of detecting and/or quantifying hybridization of target molecules to microarrays.

Several of the more common strategies for the detection of hybridization between a single-stranded oligonucleotide probe and a complementary DNA target sequence include those that involve the use of tags with characteristic properties (such as fluorescence, color, luminescence or radioactivity), gold colloids or gold colloids enhanced with silver metal, and/or microscopy, surface enhanced Raman spectroscopy, surface plasmon resonance (SPR) spectroscopy, electrochemistry, quartz crystal microbalance, scanometry, digital cameras, or light scattering. However, only some of these techniques have been applied to the high throughput screening of DNA microarrays.

Fluorescent dyes have been used in conjunction with DNA microarray technology for gene expression profiling, analysis of single nucleotide polymorphisms, genotyping, biomarker discovery, clinical diagnostics, and other applications. However, fluorescent labels suffer from drawbacks such as broad overlapping emission peaks which limit multiplexing, quenching of fluorescence, and nonuniform fluorophore photobleaching. As such, alternative fluorophore-free strategies for DNA arrays are desirable.

As an alternative to the commonly used fluorescent labels for detection of DNA hybridization, the silver-augmented gold nanoparticle strategy was applied to DNA arrays for detection on gold films by SPR or glass slides by scanometry. Quantification of the extent of hybridization in scanometry was based on the intensity of the imaged grayscale observed for the darkened silver spots.

Infrared spectroscopy has been a valuable tool for the study of bioconjugate chemistry on substrates that can either transmit (ZnSe, $CaF_2$) or reflect (gold, silver) IR light, and for the structural characterization of DNA bases and monolayers of oligonucleotide probes on gold surfaces. It was also used to qualitatively detect DNA hybridization between a single-stranded oligonucleotide probe, immobilized on the entire surface of a gold-coated slide, and its complementary synthetic target sequence. At this time, infrared microspectroscopy has not been applied to the detection of DNA microarrays primarily due to the lack of sensitivity of mercury cadmium telluride (MCT) infrared detectors (single point or focal plane array) for measuring trace amounts of biological material (DNA duplex) present in microarrayed 30 to 300 µm-diameter spots or larger on any IR substrate.

What is needed are additional fluorophore-free methods for the detection of target-capture probe hybrids on microarrays.

SUMMARY

Methods of detecting and/or quantifying hybridization of targets to microarrays on infrared absorbing substrates such as glass using mid-infrared chemical imaging (IRCI) in the external reflection mode are disclosed herein.

A method for detecting presence or absence of a target in a sample is disclosed. In an embodiment, the method comprises contacting a capture probe attached to an addressable location on a solid infrared absorbing surface with the sample under conditions effective to form a hybridization complex between the capture probe and the target, and binding to the target a mid-infrared reflective metal after contacting with the capture probe; exposing the contacted capture probe and solid surface to light having a wavenumber of 4000 $cm^{-1}$ to 900 $cm^{-1}$; and determining, in external reflection mode, any reflectance from the solid surface with the contacted capture probes, wherein measurable mid-infrared reflectance indicates the presence of the target in the sample.

A method for comparing relative quantities of a target in two or more samples is disclosed. In an embodiment, the method comprises contacting a capture probe attached to an addressable location on a solid infrared absorbing surface with a sample to be analyzed for the target under conditions effective to form a hybridization complex between the capture probe and the target, and binding to the target a mid-infrared reflective metal after contacting with the capture probe; imaging the hybridized microarray with mid-infrared radiation to produce an image and to determine relative intensity of the image for the target for the sample; repeating the contacting and imaging steps for the target in a second sample; and comparing the relative intensities of the images for the target in the two samples to determine the relative quantities of the target in the two samples.

A method for identifying a defect in a biological microarray formed on a glass substrate is also disclosed. In an embodiment, the method comprises contacting a biological microarray on a infrared absorbing substrate with a solution comprising a target to hybridize with each spot of the microarray under conditions effective to permit hybridization and binding to the target with a mid-infrared reflective metal either prior to or after contacting the microarray, wherein each spot on the microarray comprises a nucleic acid capture probe; imaging the hybridized microarray with mid-infrared radiation to produce an image; and identifying a defect in the microarrays from the spot morphology or relative reflectance intensity in the image.

These and other embodiments, advantages and features of the invention become clear when detailed description and examples are provided in subsequent sections.

BRIEF DESCRIPTION OF THE DRAWINGS

Figure 1:
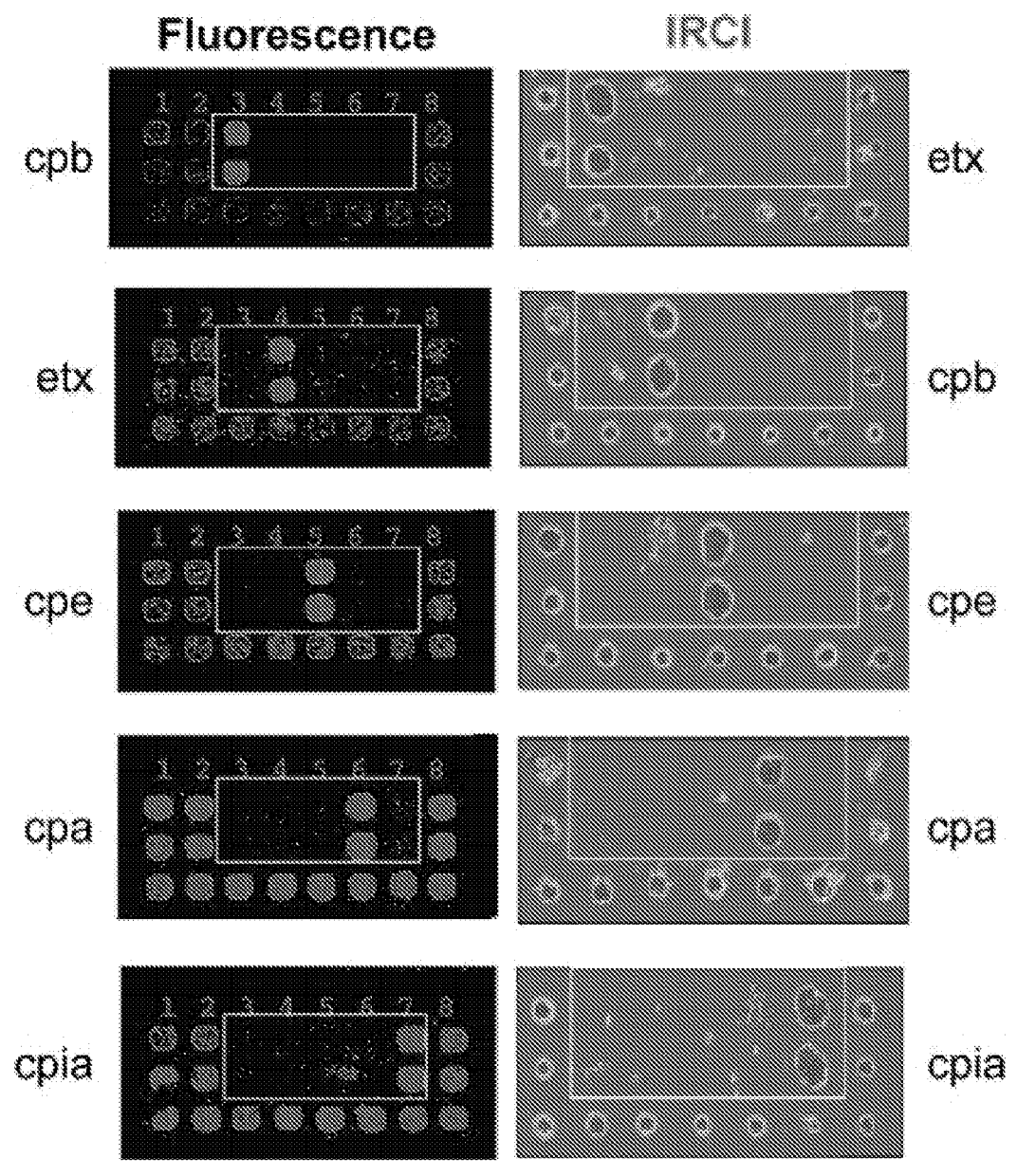

FIG. 1 shows images of DNA microarrays on glass slides (i) labeled with a fluorophore (left) and (ii) fluorophore-free (right) observed by mid-infrared chemical imaging.

FIG. 8 presents a chemical image and a histogram of relative intensity for two microarrays for detection of *C. perfringens* strains JGS1984 (upper row) and JGS1985 (bottom row) after hybridization with multiplex polymerase chain reaction products (targets).

FIG. 9 presents a histogram displaying the signal-to-noise ratio values for the 1024 pixels of a single image of a non-hybridized spot.

FIG. 10 is a schematic of the layout of microarrays for mycoplasma identification. Each microarray contains two sets of species-specific oligonucleotides.

FIG. 11 shows examples of silver-enhanced hybridization images for several *Mycoplasma* and *Acholeplasma* species detected by IRCI. Each array contains two sets of species-specific oligonucleotide probes.

FIG. 12 shows the silver enhanced hybridization image for the *M. bovis* microarray detected by IRCI. The infrared spectrum in the external reflection mode measured at each pixel of an image can be used to generate a third spectral dimension that reflects the relative intensity of spots in a microarray.

FIG. 13 shows the microarray oligoprobe layout corresponding to IRCI images of hybridized targets (FIGS. 14 and 15). The CPA gene belonging to *Clostridium perfringens* was used as a negative control. All quality control (QC) probes consisted of mixed probe sequences for the five genes investigated. Genotyping of five genes from 19 representative *Y. enterocolitica* isolates was carried out.

FIG. 14 shows a three-D infrared image for hybridized spots in an exemplary microarray for identification of *Y. enterocolitica* species.

FIG. 15 shows the quantitative IRCI microarray results for one of 19 *Y. enterocolitica* strains. Percent relative IRCI intensity values are shown on the y-axis. Three oligoprobes for each of six genes are shown on the x-axis as an average of triplicate measurements on three different days.

DETAILED DESCRIPTION

Methods of detecting and/or quantifying hybridization of targets to microarrays on infrared absorbing substrates such as glass using mid-infrared chemical imaging (IRCI) in the external reflection mode are disclosed herein. The methods provide improved signal-to-noise ratios compared to those reported for fluorescence detection of high-density arrays.

In one aspect, a method for detecting presence or absence of a target nucleic acid in a sample is disclosed. In an embodiment, the method comprises contacting a capture probe attached to an addressable location on a solid glass surface with the sample under conditions effective to form a hybridization complex between the capture probe and the target, and binding to the target a mid-infrared reflective metal either prior to or after contacting with the capture probe. By binding a mid-infrared reflective metal such as silver metal to the target, the presence or absence of the target in the sample can be detected. The method can further comprise exposing the contacted capture probe and solid surface to light having a wavenumber of 4000 $cm^{-1}$ to 900 $cm^{-1}$; and determining, in external reflection mode, any reflectance from the solid surface with the contacted capture probes, wherein measurable mid-infrared reflectance indicates the presence of the target in the sample. After cleaning of the microarray, the process can be repeated for additional samples. Relative quantities of a target present in two or more different samples can be determined by comparing the relative intensities determined for the target in the two or more different samples.

A "sample" refers to a specimen used to test for presence or absence of a target molecule.

In an embodiment, the sample is a nucleic acid sample that comprises one or more nucleic acids, e.g., oligonucleotides, which may hybridize to the capture probes attached to the solid surface. The nucleic acid sample to be assayed may be isolated by known methods, or may be detected directly in cells, tissue samples, biological fluids (e.g., saliva, urine, blood, serum), solutions containing PCR components, solutions containing large excesses of oligonucleotides or high molecular weight DNA, and other samples, as also known in the art. Methods of preparing nucleic acids for detection with hybridizing probes are well known in the art. If a nucleic acid is present in small amounts, it may be amplified by methods known in the art such as polymerase chain reaction (PCR) amplification.

The term a "target" or "target molecule" refers to a molecule of interest that is to be detected and/or analyzed, optionally quantified. A "target" as used herein refers to a molecule that has an affinity for a given capture probe. Targets may be naturally-occurring or man-made molecules. Also, they can be employed in their unaltered state or as aggregates with other species. Examples of targets which can be employed by this invention include, but are not restricted to, antibodies, proteins e.g., cell membrane receptors, drugs, oligonucleotides, nucleic acids, peptides, cofactors, lectins, sugars, polysaccharides, cells, cellular membranes, and organelles.

As used herein, "nucleic acid," "polynucleotide" and "oligonucleotide" refer to a synthetic or biologically produced molecule comprising a covalently linked sequence of nucleotides which may be joined by a phosphodiester bond between the 3' position of the pentose of one nucleotide and the 5' position of the pentose of the adjacent nucleotide. In addition, a nucleic acid, polynucleotide, or oligonucleotide may contain modified or nonnaturally occurring backbone components including phosphothioate or phosphonate or contain modified or non-naturally occurring sugar residues (e.g., arabinose) and/or modified base residues. A nucleic acid, polynucleotide, or oligonucleotide may also comprise blocking groups that prevent the interaction of the molecule with particular proteins, enzymes or substrates. A nucleic acid, polynucleotide, or oligonucleotide as used herein may therefore encompass compounds such as DNA, RNA, peptide nucleic acids, phosphothioate-containing nucleic acids, phosphonate-containing nucleic acids, and the like.

The term "capture probe" refers to a molecule that is immobilized on a solid support that binds to a target molecule for the analysis of the target. Capture probes are molecules capable of undergoing binding or molecular recognition events with target molecules. The capture probe may or may not be capable of binding to just the target molecule. Examples of capture probes include nucleic acids, polymers, proteins, and peptides.

Figure 2:
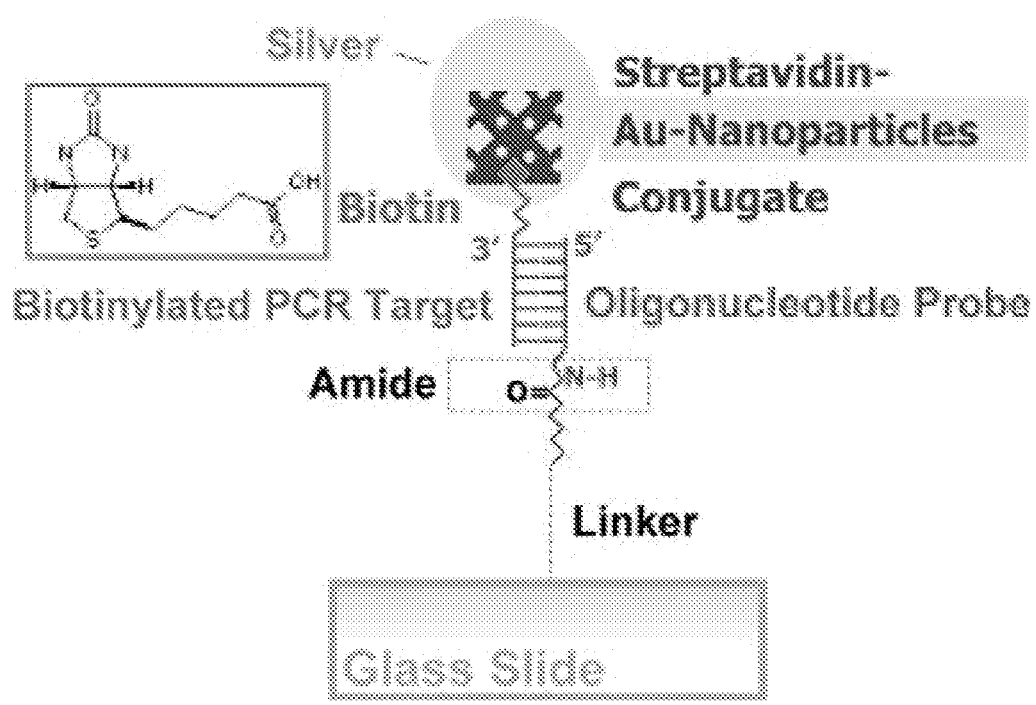
FIG. 2 presents a schematic illustration (not to scale) of the probe-target duplex structure for detection by mid-infrared chemical imaging.
Figure 3:
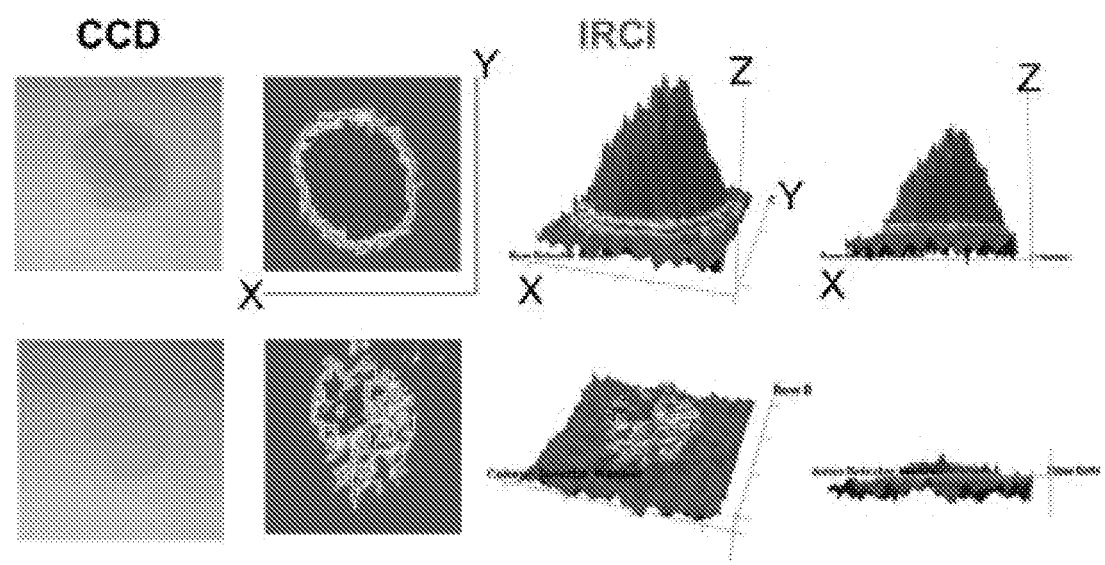
FIG. 3 compares images of a typical hybridized spot (top row) or a weak hybridized spot (bottom row) observed with a digital camera (CCD) or by mid-infrared chemical imaging (IRCI), with the Z-axis consisting of an infrared intensity spectrum at each pixel observed at 1180 cm$^{-1}$.

With respect to two nucleic acids, "hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of less than about 1M, more usually less than or equal to about 500 mM and less than or equal to about 200 mM. Hybridization temperatures can be as low as 5° C., but are typically greater than 22° C., more typically greater than about 30° C., and specifically in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the Tm for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche, and Maniatis, "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

The method comprises contacting a capture probe attached to an addressable location on a solid glass surface with the sample under conditions effective to form a hybridization complex between the capture probe and the target molecule. The capture probe attached to a solid support is in the form of a microarray, for example.

"Microarray" or "array" refers to a solid phase support having a planar surface, which carries an intentionally created collection of capture probes, each member of the array comprising copies of at least one capture probe immobilized to a spatially defined region or site on the solid phase support, which does not overlap with those of other members of the array; that is, the regions or sites are spatially discrete. Spatially defined hybridization sites may additionally be "addressable" in that its location and the identity of its immobilized capture probe are known or predetermined, for example, prior to its use. Typically, for a nucleic acid microarray, the oligonucleotides or polynucleotides are single stranded and are covalently attached to the solid phase support, usually by a 5'-end or a 3'-end. The density of non-overlapping regions containing capture probes in a microarray can depend on the particular purpose for which the microarray is designed. In some embodiments, the density of non-overlapping regions containing capture probes in a microarray is typically greater than 100 per $cm^2$, and more preferably, greater than 1000 per $cm^2$. In other embodiments, a low density of non-overlapping regions may be used. The number of non-overlapping regions present on the microarray may vary, but is generally at least 2, usually at least 10, and more usually at least 20, and may be 50, 100, 500, 1,000, 10,000 or higher, depending on the intended use of the microarray.

The microarray can also be a planar array of microbeads in which each microbead has attached a single kind of capture probe or a set of capture probes. Arrays of microbeads may be formed in a variety of ways, e.g. Brenner et al, Nature Biotechnology, 18: 630-634 (2000); Tulley et al., U.S. Pat. No. 6,133,043; Stuelpnagel et al, U.S. Pat. No. 6,396,995; Chee et al, U.S. Pat. No. 6,544,732; and the like.

Biological microarrays, such as DNA or RNA microarrays and antibody or peptide microarrays, are well known in the art. Biological microarrays can be prepared by a method known in the art. Methods for covalent attachment of nucleic acids to a solid support are known in the art. For example, nucleic acids may be attached to a solid support using methods described in the examples below. Methods for covalent attachment of antibodies or other peptides to a solid support are also known in the art. Examples of such methods are found in Bhatia, et al, Anal. Biochem. 178(2):408-413, 1989; Ahluwalia, et al, Biosens. Bioelectron. 7(3):207-214, 1992; Jonsson, et al, Biochem. J. 227(2):373-378, 1985; and Freij-Larsson, et al, Biomaterials 17(22):2199-2207, 1996.

"Substrate," "support" and "solid support" refer to a material or group of materials having a rigid or semi-rigid surface or surfaces. Examples of materials include plastics (e.g., polycarbonate), complex carbohydrates (e.g., agarose and sepharose), acrylic resins (e.g., polyacrylamide and latex beads), nitrocellulose, glass, silicon wafers, and positively charged nylon. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations. The substrate is specifically an infrared absorbing substrate.

Methods for creating microarrays are known in the art, including printing on a solid support using pins (passive pins, quill pins, and the like) or spotting with individual drops of solution. Passive pins draw up enough sample to dispense a single spot. Quill pins draw up enough liquid to dispense multiple spots. Bubble printers use a loop to capture a small volume which is dispensed by pushing a rod through the loop. Microdispensing uses a syringe mechanism to deliver multiple spots of a fixed volume. In addition, solid supports can be arrayed using piezoelectric (ink jet) technology, which actively transfers samples to t solid support. Suitable concentrations of nucleic acid range from about 1 ng/µl to about 1 µg/µl. In some embodiments, each spot can contain one or more than one distinct nucleic acid.

Other methods of creating arrays are known in the art, including photolithographic printing (Pease, et al., PNAS 91(11):5022-5026, 1994) and in situ synthesis. For example, nucleic acids can be synthesized residue by residue on compartmentalized regions on a silicon substrate using photolithography techniques used in the production of semiconductor chips (U.S. Pat. No. 5,445,934; U.S. Pat. No. 5,774,305). Oligonucleotide microarrays can also be made by techniques including "spotting," depositing either single nucleotides for in situ synthesis of oligonucleotides or completed oligonucleotides by physical means (ink jet printing and the like), electrochemical in situ synthesis based upon pH based removal of blocking chemical functional groups (U.S. Pat. No. 6,092, 302), and electric field attraction/repulsion of fully-formed oligonucleotides (U.S. Pat. No. 5,653,939).

Once the sample is contacted with the capture probe, the presence or absence of the target in the sample is detected. In order to detect the presence or absence of the target in the sample, the targets in the sample are bound to a mid-infrared reflective metal either prior to or after contacting with the capture probes. Mid-infrared reflective metals include silver metal, copper, aluminum and chromium.

In one embodiment, in order to detect the presence or absence of targets in the sample, the targets in the sample are conjugated to a nanoparticle such as a gold nanoparticle. Exemplary nanoparticles include metal (e.g., gold, silver, copper and platinum), semiconductor (e.g., CdSe, CdS, and CdS or CdSe coated with ZnS) and magnetic (e.g., ferromagnetite) colloidal materials. Other exemplary nanoparticles include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is about 5 nm to about 150 nm (mean diameter), more specifically about 5 to about 50 nm, most specifically about 10 to about 30 nm. The nanoparticles may also be rods.

In one embodiment, the nanoparticle is a gold nanoparticle. Suitable nanoparticles are also commercially available from, e.g., Ted Pella, Inc., Amersham Corporation and Nanoprobes, Inc.

In one embodiment, the nanoparticle is conjugated to the target prior to contacting with the capture probe, through a covalent or noncovalent bond. In this embodiment, the nanoparticles, the targets (e.g., nucleic acids) or both are functionalized in order to attach the target to the nanoparticles. For instance, nucleic acids functionalized with alkanethiols at their 3'-termini or 5'-termini readily attach to gold nanoparticles. The alkanethiol method can also be used to attach nucleic acids to other metals and to the other nanoparticles listed above. Other functional groups for attaching nucleic acids to nanoparticles include phosphorothioate groups, and substituted alkylsiloxanes. Oligonucleotides terminated with a 5' thionucleoside or a 3' thionucleoside may also be used for attaching nucleic acids to nanoparticles.

In one embodiment, the nanoparticle is conjugated to the targets in the sample, e.g., the target nucleic acids, after contacting the sample with the capture probe. In a specific embodiment, the nucleic acids in a nucleic acid sample are biotinylated prior to contacting with the capture probes. If a target nucleic acid in the nucleic acid sample is complementary to a capture probe, the target nucleic acid will hybridize to the capture probe to form a hybridization complex. Non-hybridized sequences are removed, for example, by washing. Then the hybridization complexes will be contacted with streptavidin conjugated to a nanoparticle. The streptavidin hybridizes to the biotin on the target sequence thus conjugating the nanoparticle, e.g., a gold nanoparticle, to the target sequence. Unbound streptavidin is removed, for example, by washing, so that the presence of the target nucleic acid is determined by detecting the presence of the nanoparticle.

As alternatives to biotin/streptavidin for gold nanoparticle labeling of targets, biotin can also be paired with gold-labeled avidin, neutravidin, captavidin, or anti-biotin antibodies labeled with gold. Digoxigenin and dinitrophenyl can be captured using gold-labeled antibodies specific for the respective hapten.

If the nanoparticle itself is not mid-infrared reflective, the mid-infrared reflectivity can be provided by enhancing the signal with a mid-infrared reflective metal such as silver, aluminum, copper or chromium. In one embodiment, silver enhancement is employed. Optionally, silver enhancement of the nanoparticle signal is employed prior to detection of the target sequences. In a silver enhancement protocol, metallic silver is deposited onto the surface of the nanoparticle, e.g., a gold nanoparticle, which enhances the signal to be detected by mid-IR spectroscopy. In the protocol, the microarray is contacted with silver ions and the silver ions are selectively reduced to silver metal at the surface of the gold nanoparticles, for example. Exemplary reducing agents include, for example, hydroquinone. The hybridized spots, particularly when enhanced with silver, become effective infrared substrates that reflect sufficient infrared radiation to enable mid-infrared detection.

Once the hybridization complexes, if present, are formed, the surface of the substrate is imaged using mid-infrared imaging in the external reflection mode. In mid-infrared imaging, the contacted capture probe and solid surface are exposed to light having a wavenumber of 4000 $cm^{-1}$ to 900 $cm^{-1}$; and determining any measurable mid-infrared reflectance from the solid surface in external reflection mode. The measurement of reflectance indicates the presence of the target nucleic acid in the sample.

Mid-infrared imaging in the external reflection mode is distinct from the more typical fluorescence imaging. In a fluorescence imaging experiment, the presence of a fluorophore in a hybridization complex is determined by exposing the surface to a wavelength of light that is absorbed by the fluorophore and then measuring emission of fluorescence as the fluorochrome falls from its excited state to the ground state. Drawbacks of the use of fluorescent labels include broad overlapping emission peaks which limit multiplexing, quenching of fluorescence, and nonuniform fluorophore bleaching. Mid-infrared imaging in the external reflection mode is a fluorophore-free method in which a surface is exposed to mid-infrared radiation and the radiation that is reflected off of the surface is measured. Reflectance is the fraction of incident electromagnetic radiation that is reflected at an interface. In this method, the hybridized target molecules bound to mid-infrared reflective metals provide a spectral image that can be detected in the external reflection mode, while the unhybridized nucleic acid and streptavidin do not provide an image.

In this method, Fourier transform mid-infrared (FTIR) microspectroscopy can be combined with qualitative detection of bound mid-infrared reflective metals using a digital camera. In one embodiment, detection of DNA hybrids is performed by focal plane array Fourier transform mid-infrared (FTIR) microspectroscopy. Focal plane arrays (FPA) are detectors which consist of a linear or two-dimensional matrix of individual elements. They are used at the focus of imaging systems. This chemical imaging method generates a third artificial dimension, the z-axis, that is a mid-infrared spectrum at each pixel in an image. In one embodiment, by using a single-element mercury cadmium telluride (MCT) focal plane infrared detector, with mid-infrared imaging in the external reflection mode, it is possible to both detect and quantify DNA microarray hybridization on glass slides. In one embodiment, detection of hybrids is formed using an FTIR spectrometer in communication with an infrared microscope and a focal-plane array detector such as an MCT detector. Not only can non-hybridized spots be distinguished from hybridized spots, but hybridization can be quantified by measuring the integrated intensity over a selected spatial range defined by pixels over a hybridized spot.

The method can also be used to identify specific proteins or peptides in a sample. For example, an antibody array used to identify the presence or absence of specific target antigens are contacted with a sample to be tested for one or more antigens based on binding specificity to antibodies in the array. The antigens are often proteins, although they may also be organic chemical compounds, carbohydrates, nucleic acids, and the like. They may be isolated or semi-isolated, recombinant or naturally occurring. The amount of antigen used can vary from about 1-100 ng/μl. The antigen is left in contact with the array for an amount of time sufficient for antibody:antigen complexes to form, should one of the antibodies in the array be specific for any antigen in the sample. The amount of time sufficient for this purpose will range from 5 minutes to 24 hours, and will generally be from 0.5 to 2 hours.

In another aspect, a method for identifying a defect in a nucleic acid microarray formed on a glass substrate is provided. In an embodiment, the method comprises contacting a nucleic acid microarray on a glass substrate with a solution comprising a target nucleic acid to hybridize with each spot of the microarray under conditions effective to permit hybridization, and binding to the target nucleic acid a mid-infrared reflective metal either prior to or after contacting the microarray, wherein each spot on the microarray comprises a capture probe; imaging the hybridized microarray with mid-infrared radiation to produce an image; and identifying a defect in the microarrays from the spot morphology in the image. A missing spot in the image corresponds to a defect of a missing spot on the microarray. An irregularly shaped spot in the image identifies an irregularly shaped spot on the microarray. An image of a spot with higher relative reflectance intensity around the perimeter of the spot and lower relative reflectance intensity in the middle of the spot identifies a defect of lower probe concentration in the center of the spot than at the perimeter of the spot.

The invention is further illustrated by the following non-limiting examples:

EXAMPLES

Example 1

Preparation of Bacterial Strains and Oligonucleotides

Bacterial strains and growth. A trypticase-peptone-glucose-yeast (TPGY) extract medium was used to grow the *C. perfringens* strains investigated in the present study according to published procedures. Briefly, the TPGY medium was boiled for 10 minutes to eliminate dissolved air and cooled to room temperature before inoculation. Inoculated medium tubes were incubated at 35° C. aerobically for 16-24 hours. Genomic DNA was isolated using a Puregene® DNA Isolation Kit (Gentra Systems, Minneapolis, Minn.) and by cold shocking cells three times in dry ice followed by treatment of cells with 50 μl of 10 mg/ml lysozyme solution for 30 min at 37° C. The DNAzol® Genomic DNA Isolation Kit (Molecular Research Center, Cincinnati, Ohio) was also used.

Design of PCR primer and gene-specific oligonucleotide capture probes. Primers were adapted from the prior art and oligonucleotide probe sequences were designed to complement the non-biotin-labeled reverse primer strands. A homology search of the GenBank database was done using the Basic Local Alignment Search Tool (BLAST) to confirm the uniqueness of the sequences. Each oligonucleotide probe sequence was attached to an amino group at the 3' end to allow covalent bonding to the glass slides pre-functionalized with succinimidyl ester groups (SurModics, Eden Prairie, Minn.). Probe sequence design for each gene (Table 1) was carried out by using ArrayDesigner (Premier Biosoft International, Palo Alto, Calif.) software. All DNA oligonucleotide probes and complementary synthetic targets were synthesized by Alpha DNA (Montreal, Canada). The biotin-labeled forward primer oligonucleotides were synthesized by Operon Technologies (Alameda, Calif.).

Single polymerase chain reaction (PCR) amplification of five *C. perfringens* genes. The PCR mixture (50 μl) used consisted of 14 pmol of each primer, about 300 ng of DNA template, and 25 μl of HotStarTaq™ DNA polymerase master mix. Following an initial incubation at 95° C. for 5 min, target amplification was achieved by using 35 cycles at 94° C. for 25 s, 55° C. for 25 s, 72° C. for 30 s, and terminated with a cycle at 72° C. for 15-min incubation. Gel electrophoresis using a 2% agarose gel was carried out to verify the PCR products and determine their molecular weights.

Multiplex PCR amplification. The standard PCR mixture (50 μl) contained 1× reaction buffer with 4 mM $MgCl_2$, 500 ng of DNA template, and 25 μl of master mix of HotStarTaq™ DNA polymerase (Quiagen, Inc., Valencia, Calif.). A negative PCR amplification control lacking DNA template was included in the experiment. The following conditions were used for PCR amplification: initial enzyme activation at 95° C. for 5 min, 35 cycles at 94° C. for 25 s, 52° C. for 25 s, 72° C. for 30 s, and final elongation at 72° C. for 5 min.

Preparation of biotinylated PCR products (targets). Single-stranded DNA (ssDNA) was prepared from double stranded amplicons using Dynabeads® M-280 Streptavidin reagent (Invitrogen, Carlsbad, Calif.) according to the manufacturer's protocol. Briefly, 50 μl of magnetic bead suspension in 2× binding buffer consisting of 10 mM Tris-HCl, pH 7.5, 1 mM ethylenediaminetetraacetic acid (EDTA), and 2 M NaCl were added directly to the PCR reaction. The mixture was incubated at room temperature for 30 min with intense agitation. Magnetic beads with the bound PCR products were separated from the solution using a magnetic particle concentrator MPC-S (Invitrogen) and washed once with 1× binding buffer. The ssDNA was eluted from the beads using 50 μl of 0.1M NaOH. After pH neutralization by addition of 5 μl of 3 M sodium acetate (pH 5.8), ssDNA was additionally purified using the CentriSep® column (Princeton Separations, Adelphia, N.J.) equilibrated with deionized water. The purified ssDNA was biotinylated using Label It® Biotin Labeling Kit (Mirus Bio, Madison, Wis.) according to the manufacturer's protocol. Briefly, a 50-μl reaction mixture contained 1× Minis labeling buffer, 0.1 to 0.5 μg of ssDNA, and 3-5 μl of Mirus Label It® Biotin reagent. Reaction was carried out at 37° C. for 1 h. DNA was additionally denatured by using reagents provided with the labeling kit. After denaturing, biotinylated DNA samples were cleaned-up using the water-equilibrated CentriSep® columns, dried under vacuum, and reconstituted in the Micromax hybridization buffer III (Perkin-Elmer, Boston, Mass.) at a final concentration of 0.05 μM.

Example 2

Microarray Printing

Microarrays were printed using a PixSys™ 5000 contact microspotting robotic system (Cartesian Technologies, Irvine, Calif.). The average size of a spot was 120 μm. The concentration of the oligonucleotide probes before printing was adjusted to 90 μM in borate buffer pH 8.5. Printed glass slides (SurModics) were incubated in a humidity chamber at room temperature overnight. The slides were placed in a staining jar containing 50 mM ethanolamine blocking solution that had been pre-warmed to 50° C. for 30 min. The slide was rinsed with deionized water and then placed in a staining jar containing 4× saline sodium citrate (SSC) and 0.1% sodium dodecyl sulfate (SDS) washing solution that had been pre-warmed to 50° C. The jar was then placed in a shaker at 120 rpm for 30 min. The slide was rinsed with deionized water and spun dry at 800 rpm for 3 min.

Fabrication of DNA microarrays on gold-coated slides was also carried out. A self-assembled monolayer of thiolated succinimidyl ester was first generated over the entire surface of the gold coated-slide. Subsequently amine-modified oligonucleotide probes were printed to the surface, as described above.

Example 3

Microarray Hybridization and Imaging

Hybridization of biotinylated DNA samples to the microarray was carried out in a hybridization chamber that was placed in an incubator at 45° C. for 1 hour. Each sample was placed on the glass slide and covered with a glass cover-slip (Erie Scientific, Portsmouth, N.H.) to prevent evaporation of the target during incubation. After hybridization, the slides were washed once for 1 min with 6×SSC containing 0.4% gelatin and 0.1% Tween 20, then three times each for 30 s with 6×SSC buffer followed by centrifugation at 800 rpm for 3 min to remove any traces of the buffer. After hybridization, each array was incubated with 6 µl of solution containing 5-nm gold-labeled streptavidin (Kirkegaard and Perry Laboratories, Gaithersburg, Md.), diluted 1:5 (v/v) with 6×SSC buffer containing 0.4% gelatin and 0.1% Tween 20. The incubation was carried out at room temperature for 30 min. The slides were washed once with 6×SSC solution containing 0.1% Tween 20, then twice with 6×SSC, and twice with 0.6 M $NaNO_3$ followed by centrifugation at 800 rpm for 3 min to remove traces of buffers. Subsequently, silver enhancement was conducted using reagents A and B optimized for microarray applications and provided by Ted Pella, Inc. (Redding, Calif.). The slides were incubated with the 1:1 (v/v) mixture of the reagents A and B for 10 min followed by multiple washing with deionized water, and spin drying at 800 rpm for 3 min.

Mid-infrared imaging of DNA microarrays. Spectral images were collected with a Varian FTIR spectrometer model 7000e operating under Varian Resolution Pro 4.0 software (Varian, Melbourne, Australia) and equipped with a UMA 600 infrared microscope and a 32×32 (or 1024) pixels MCT focal-plane-array detector. A continuous flow of dry air was used to purge the spectrometer and microscope to minimize the levels of atmospheric carbon dioxide and water vapor. Each spectral image was obtained from approximately a 180×180 µm$^2$ test sample area with a nominal spatial resolution of 5.6 µm per pixel and a spectral resolution of 8 cm$^{-1}$. For each image 16 co-added scans were collected and required approximately 16 sec of acquisition time. The generated infrared image data were analyzed using the Varian Resolution Pro 4.0 software as well as the ISys (release 3.1) software (Malvern Instrument Ltd, Worcestershire, UK). Individual chemical images collected for hybridized and non-hybridized spots in a given microarray were subsequently "quilted" together to produce an image of the entire microarray by using Microsoft PowerPoint. Visual image collection was carried out by using a CCD camera that was integrated with the UMA 600 microscope just before each test sample IR data collection.

Example 4

Silicate Glass as IR Absorbing Substrate

Glass slides have almost exclusively been used in molecular biology as solid transparent substrates for spotting DNA microarrays because silicate glass can be chemically functionalized with materials that allow the immobilization of oligonucleotide probes and do not interfere with the detection of fluorescent labels (FIG. 1). Since glass is not a typical mid-infrared substrate, glass slides were evaluated in the present study and found to be suitable for the detection of DNA microarrays by mid-infrared chemical imaging (IRCI).

FIG. 1 shows images of DNA microarrays for detecting five representative *C. perfringens* genes, the virulence genes cpb, etx, cpe, cpa, and cpia, detected by fluorescence (left panels) and IRCI (right panels).

Microarrays of synthetic alkyl amine-modified oligonucleotide capture probes were spotted on glass microscope slides pre-functionalized with succinimidyl ester groups to produce a monolayer of single-stranded oligonucleotide probes that are immobilized via a covalent amide linkage. In this study of IRCI microarray hybridization detection, biotinylated targets consisting of synthetic oligonucleotides or polymerase chain reaction (PCR) products in buffer solution can be selectively hybridized to their complementary microarrayed probes. The PCR amplified DNA products tested herein are isolated from *C. perfringens*. Gold nanoparticle (5-nm)-streptavidin conjugates were subsequently allowed to bind to the biotin groups. To visualize the selectively hybridized DNA spots, silver ions were added to the slides, and their chemical reduction to silver metal was promoted at the surfaces of the gold nanoparticles. Since only hybridized spots were selectively augmented with silver metal, only the hybridized spots were effectively infrared substrates that reflected sufficient radiation to enable infrared detection. IRCI permitted the differentiation between hybridized and non-hybridized spots. The most distinctive mid-infrared chemical images with maximum contrast were measured at 8 $cm^{-1}$ resolution at a discrete wavenumber (1180 $cm^{-1}$) for all pixels over a hybridized DNA spot in an image.

FIG. 2 provides a schematic illustration of the probe-target duplex structure for detection by mid-infrared chemical imaging. This particular hybridization product was generated by the following strategy: (1) immobilization of amine-modified oligonucleotide probes on a glass slide prefunctionalized with succinimidyl ester groups via the formation of covalent amide bonds, (2) selective hybridization of probes to their complementary biotinylated targets, (3) binding of biotin to streptavidin-gold nanoparticle conjugates, and (4) silver enhancement of nanoparticles. Silver is highly reflective in the infrared region. Raman depth profiling data showed that the resulting double stranded DNA duplex and the DNA/biotin/streptavidin biological complex are each only several nanometers thick, while the thickness of the silver layer is in the micrometer range.

In each of the arrays in FIG. 1, each spot inside the white rectangle drawn in each array resulted from selective hybridization of a complementary target to an immobilized oligonucleotide probe sequence for one of the five representative *C. perfringens* genes tested. Oligonucleotide probe sequences for the represented genes are given in Table 1.

TABLE I

Amine-modified probe sequences for the *C. perfringens* genes investigated

Figure 4:
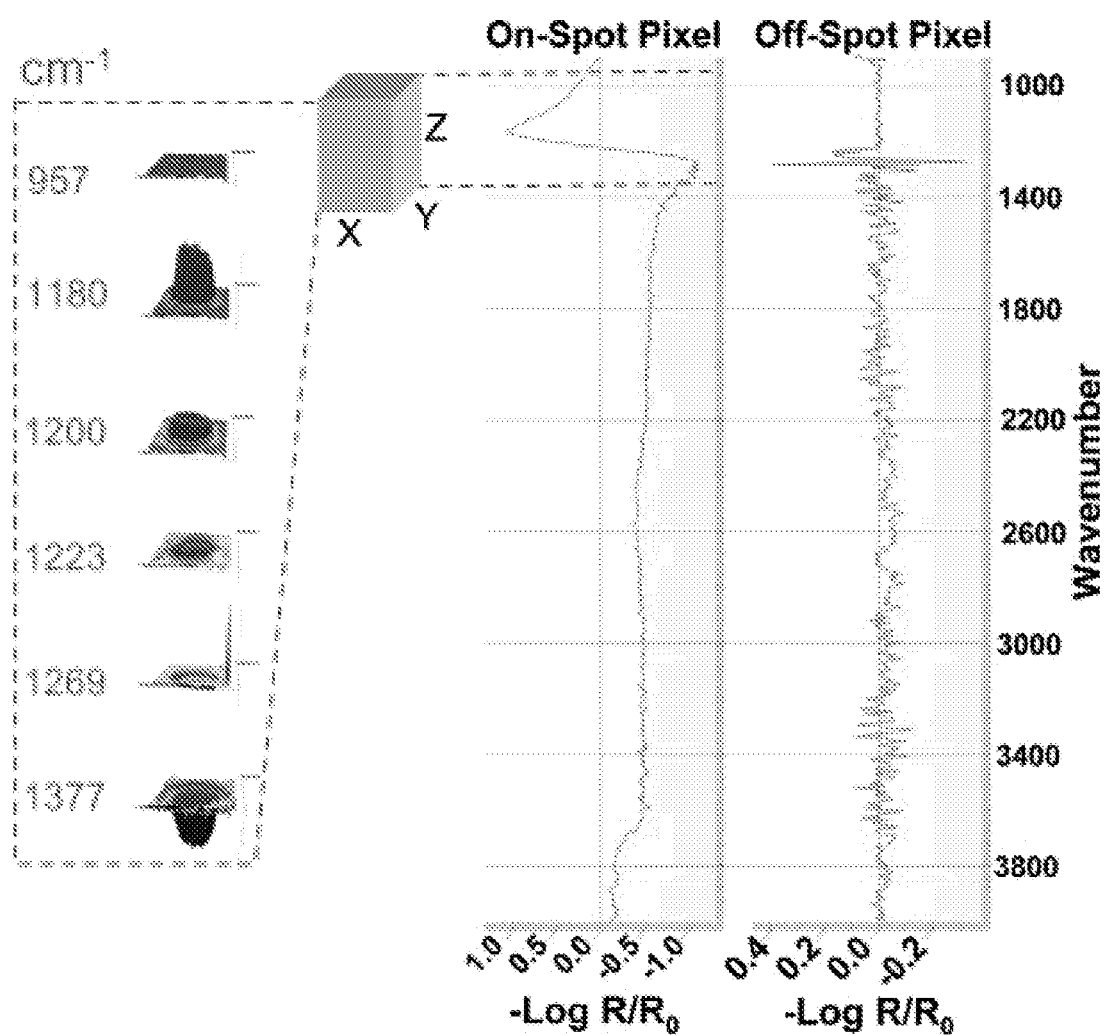
FIG. 4 shows a representation of an infrared chemical image as a hyperspectral image cube, in which X and Y are the spatial dimensions and Z is the third artificial dimension that consists of infrared spectra (center); unique images observed at various wavenumbers (left); and two typical spectra (right) observed for a single pixel that is spatially located on a spot or a single pixel that is spatially located off a spot.

| Gene | Oligonucleotide sequence | SEQ ID NO. | Location | Annealing T (° C.) |
|---|---|---|---|---|
| cpb | ACAGACAGATCATTCAACCTCT | 1 | 926-947 | 51 |
| etx | AGTTGAATTAGATGGAGAACCA | 2 | 518-535 | 49.1 |
| cpe | GGAACCCTCAGTAGTTTCAAGT | 3 | 213-234 | 52.9 |
| cpa | AGCATGAGTCATAGTTGGGATG | 4 | 1493-1514 | 52.9 |
| cpia | TGAGTCTCCAGAGAAATTTGCG | 5 | 1869-1890 | 52.9 |

Two replicate spots for each gene were printed in each array. Synthetic as well as polymerase chain reaction targets yielded similar results.

Chemical images (right) were observed for biotinylated targets bound to gold nanoparticles-streptavidin conjugates in which the size of the nanoparticles was selectively enhanced with highly reflective silver metal. All the unmarked spots (outside a white rectangle) are quality control (QC) probes which consisted of mixed probe sequences for the five genes investigated. The observed control spot size was approximately 70 μm in diameter, probably because only the microarray was exposed to only one target sequence so only one of the five control probe sequence components in each spot would have a hybridization target. Test spots inside the white rectangles were approximately 120 μm in diameter.

Using the strategy shown in FIG. 2 in which only hybridized spots on the microarrays on glass slides were selectively enhanced with silver metal resulted in high detectability of the hybridization spots by IRCI. Commercially available silicate glass slides were used as the infrared-absorbing substrates for generating an IR spectrum at every pixel located over the silver-enhanced area in chemical images of hybridized spots. The spatial resolution in a mid-IR spectrum, which will vary between approximately 5 μm to 30 μm depending on wavenumber, was found to be adequate for measuring DNA microarrays in the present study.

FIG. 1 shows that images of the DNA microarrays on glass for the five *C. perfringens* virulence genes detected by fluorescence or IRCI were qualitatively similar, indicating that IRCI is a viable alternative detection method because it provides the same information obtained by fluorescence-based detection.

The silver enhancement protocol described herein was also tested with microarrays on gold-coated slides. Poor mid-infrared image contrast was obtained when hybridized silver spots were measured relative to a gold surface.

IRCI detection of nucleic acid was also attempted with the microarrays on gold-coated slides in the absence of the silver enhancement protocol. In the absence of the silver enhancement protocol, the DNA (single stranded or double stranded) in a 120 μm-diameter spot was undetectable by ICRI.

Example 5

Mid-IR Spectra and Chemical Images

A number of experimental factors may give rise to a weak hybridization spot including non-selective binding, instrumentation problems, and/or analyst error. FIG. 3 compares images of a typical hybridized spot (top row) or a weak hybridized spot (bottom row) observed with a digital camera (CCD) or by mid-infrared chemical imaging (IRCI), with the Z-axis consisting of an infrared intensity spectrum at each pixel observed at 1180 $cm^{-1}$. As shown in FIG. 3, only hybridized spots have significant intensity along the z-axis, so weak spots can be readily distinguished from hybridized spots by measuring intensity along the z-axis.

Images collected for microarrayed spots were ratioed against, i.e., measured relative to, a background area on the slide located adjacent to a microarray. A bare portion of the glass slide was used for measuring reference background single beam spectra in order to maximize the qualitative and quantitative differences between spectra observed for hybridized and non-hybridized microarrayed spots.

FIG. 4 illustrates an infrared chemical image (IRC) represented as a hyperspectral image cube, in which X and Y are the spatial dimensions and Z is the third artificial dimension consisting of infrared spectra. For each pixel in an image, the intensity at a given wavenumber is displayed. On the left of FIG. 4 are unique IRC images observed at various wavenumbers between approximately 1400 $cm^{-1}$ and 950 $cm^{-1}$. On the right of FIG. 4 are two spectra observed for a single pixel that is spatially located on a spot or a single pixel that is spatially located off a spot, respectively.

The observed mid-infrared spectra shown in FIG. 4 (right side) exhibited both negative and positive bands. As this is uncommon, band assignment was not expected to be achieved by comparison to spectra in traditional mid-infrared libraries.

In FIG. 4, a typical infrared spectrum observed in the external reflection mode is displayed as $-\log(R/R_0)$, the reflection analogue of optical absorbance, vs. wavenumber for a single on-spot pixel from a hybridized, silver-augmented spot. For this case, R is the reflectance of a test sample (e.g., silver spot) on a glass slide, and $R_0$ is the reflectance measured at a location adjacent to a microarray on the same glass slide. In this case, silver metal did not produce an infrared spectrum, while the slide's silicate glass background reference material was expected to give rise to negative infrared bands. The biomolecules in a spot, DNA and streptavidin, did not interact with infrared radiation in the external reflection mode. Without being bound by theory, this may be because the biomolecules were shielded by the outer reflective silver shell in a spot. The prominent infrared band observed between 1500 $cm^{-1}$ and 1000 $cm^{-1}$ is attributed to the silicate Si—O stretching vibration. A negative feature was observed with an apparent minimum near 1300 $cm^{-1}$ (see on-spot pixel spectrum in FIG. 4). The wavenumber of this minimum is a transition point below which diffuse reflection was minimized and specular reflection became dominant. As illustrated in FIG. 5, diffuse reflection is used to refer to the components of collected radiation that have penetrated into the glass slide, while specular reflection is the mirror-like reflection of radiation from a surface, in which radiation from a single incoming direction is reflected into a single outgoing direction. A specular reflection component usually leads to anomalous dispersion that results in distortion in infrared band shape and, if the absorptivity were large, would lead to band inversion (*Reststrahlen* bands). In the present study, an intense, inverted and broad band with a maximum near approximately 1180 $cm^{-1}$ attributed to the Si—O linkage was observed, as shown in FIG. 4 in the spectrum for an on-spot pixel.

For a given silver spot, many different images are collected in the infrared external reflection mode because the images were found to be strongly dependent on wavenumber (FIG. 4, far left). The two most prominent images for spots were those observed below approximately 1200 $cm^{-1}$ which consisted of positive three-dimensional (3D) peaks, while those obtained above approximately 1300 $cm^{-1}$ appeared as negative 3D peaks. The series of images observed between approximately 1400 and 950 cm$^{-1}$ (FIG. 4, left) clearly illustrate a trend attributed to a transition occurring near 1250 cm$^{-1}$ between diffuse and specular reflection modes. Diffuse reflectance results in images of negative intensity ("holes"), while specular reflection results in images of positive intensity peaks. For instance, at 1269 cm$^{-1}$ the negative 3D peak has nearly disappeared and a localized sharp positive spike due to reflection from a single or a few localized pixels, reportedly highly characteristic of specular reflection, was observed. However, at 1223 cm$^{-1}$, a positive peak is beginning to emerge at the outer rim of a spot, and at 1200 cm$^{-1}$ a significant increase in the formation of a positive peak could be detected.

Example 6

Diffuse and Specular Reflection Modes

Figure 5:
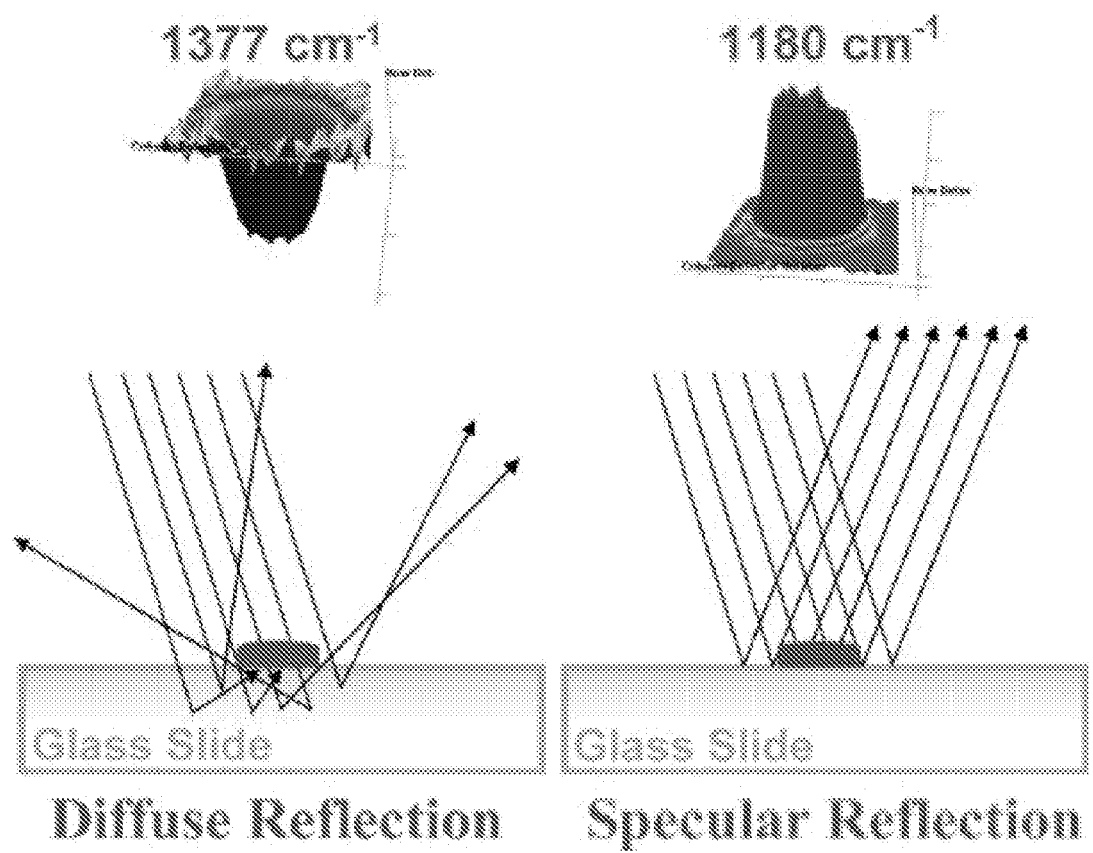
FIG. 5 presents schematic diagrams representing diffuse and specular external reflection modes and corresponding chemical images observed at wavenumbers associated with these two distinct phenomena.

FIG. 5 presents chemical images observed at wavenumbers associated with diffuse and specular reflection modes. IRCI measurement in the transmission mode (unpublished data) indicated that refraction (transmission) through the glass slide occurred above approximately 2300 cm$^{-1}$.

The infrared beam with wavelengths longer than 7.7 μm (starting below 1300 cm$^{-1}$) was specularly reflected by the outer surface of the slide, and a highly reflective silver spot appeared by IRCI as a positive 3D peak above the slide background (FIG. 5). By contrast, diffuse reflection occurred at wavelengths shorter than 7.7 μm. In this case, the focused infrared beam was projected into the glass slide where it was partly reflected, scattered, refracted (transmitted) through the slide, and absorbed by silicate. Some of this diffusely scattered light was back reflected and measured by the focal plane array detector, unless an opaque silver spot obscured its path. A negative 3D peak (dark hole) was observed by IRCI whenever a silver spot eclipsed this back-reflected light (FIG. 5). The extent of hybridization and opaqueness of a silver spot appeared to be directly correlated with the Si—O stretching band intensity. In the absence of hybridization and silver metal, no infrared band was observed and an image with no peak was obtained. The sharp noise spikes observed in the spectrum for the off-spot pixel in FIG. 4 (far right) were found to be near the transition point between diffuse reflection and specular reflection.

Example 7

Qualitative Image Analysis Tool

Figure 6:
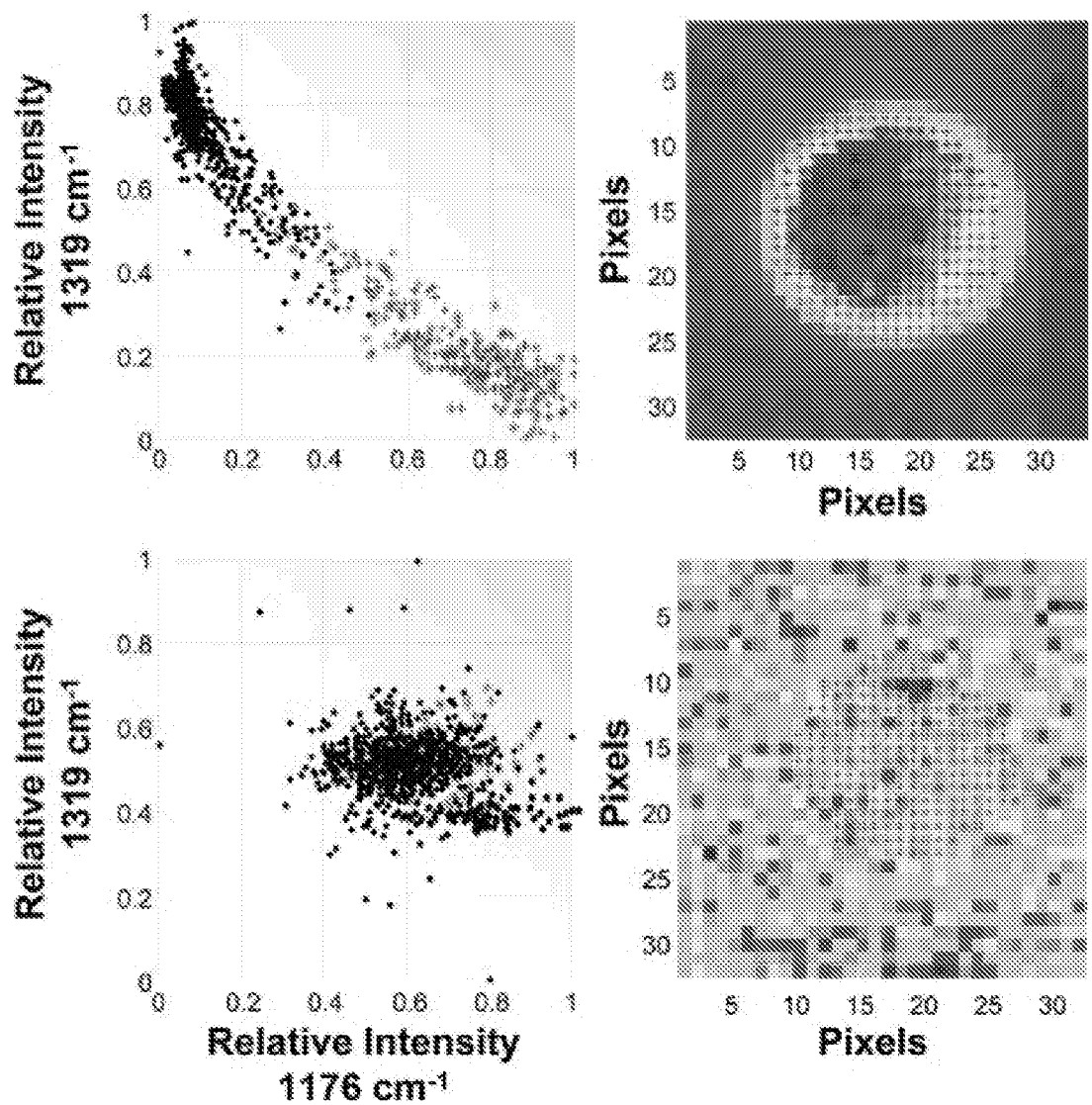
FIG. 6 presents a chemical image and a scatter plot of relative intensities observed at 1319 and 1176 cm$^{-1}$ for all 1024 pixels of the chemical image for a hybridized spot (top row) and a non-hybridized spot (bottom row).

A scatter plot is a convenient tool to detect hybridization qualitatively. FIG. 6 presents a chemical image and a scatter plot of relative intensities observed at 1319 and 1176 cm$^{-1}$ for all 1024 pixels of the chemical image for a hybridized spot (top row) and a non-hybridized spot (bottom row). The wavenumbers 1319 and 1176 cm$^{-1}$ correspond approximately to the wavenumbers of the maximum (1176 cm$^{-1}$) and minimum (1319 cm$^{-1}$) intensity values observed in a spectrum from a hybridized spot. (See FIG. 4 on-spot spectrum) If the probes in a spot are hybridized to the target, spot images of a positive peak and a negative hole are produced at these two wavenumbers, respectively.

The plus signs in the scatter plot represent image pixels indicating hybridization intensities, while the black dots denote the remaining pixels. The pixels (plus signs) which indicate the location of a hybridized intensity signal were separated from the pixels (black circles) indicating the location of a nonhybridized intensity signal only when probes in the spot are hybridized (FIG. 6, top image and scatter plot). In the absence of hybridization to the probes in a spot, no segregation of pixels was observed in the resulting scatter plot (bottom scatter plot and image in FIG. 6).

These results indicate that IRCI can be used to distinguish between hybridized and non-hybridized spots on a nucleic acid microarray.

Example 8

DNA Spot Quality Evaluation by IRCI

Many known limitations have been well documented to occur during the fabrication of microarrays or the various steps of hybridization assays. IRCI information about spot morphology proved to be useful in characterizing and optimizing fabrication and analysis of DNA microarrays.

Figure 7:
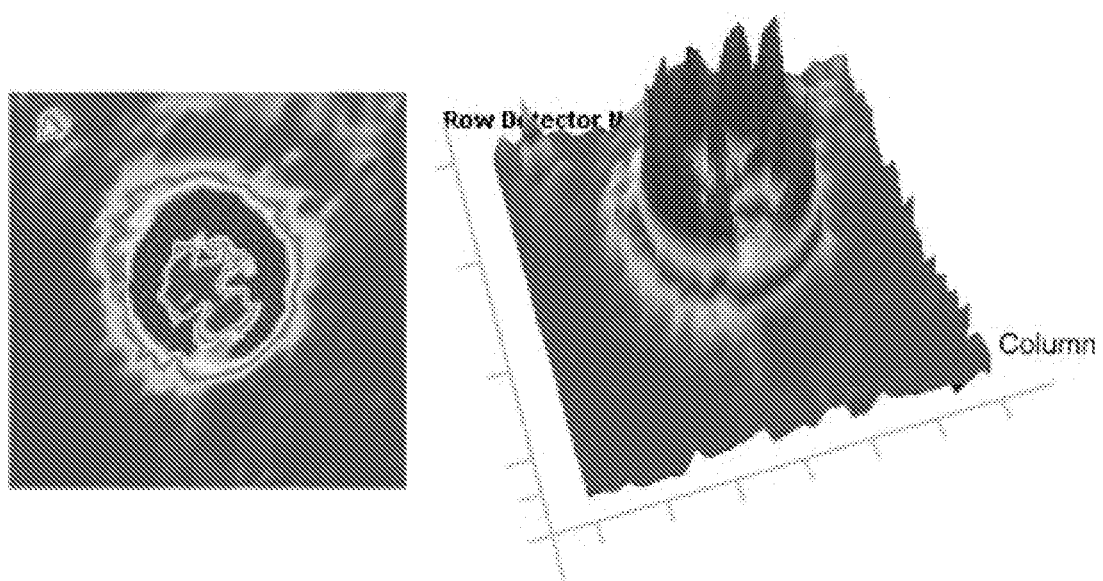
FIG. 7 presents chemical images of a microarray spot, consisting of an open circle instead of a solid circle (or peak), revealing a defect in the spot.
Figure 9:
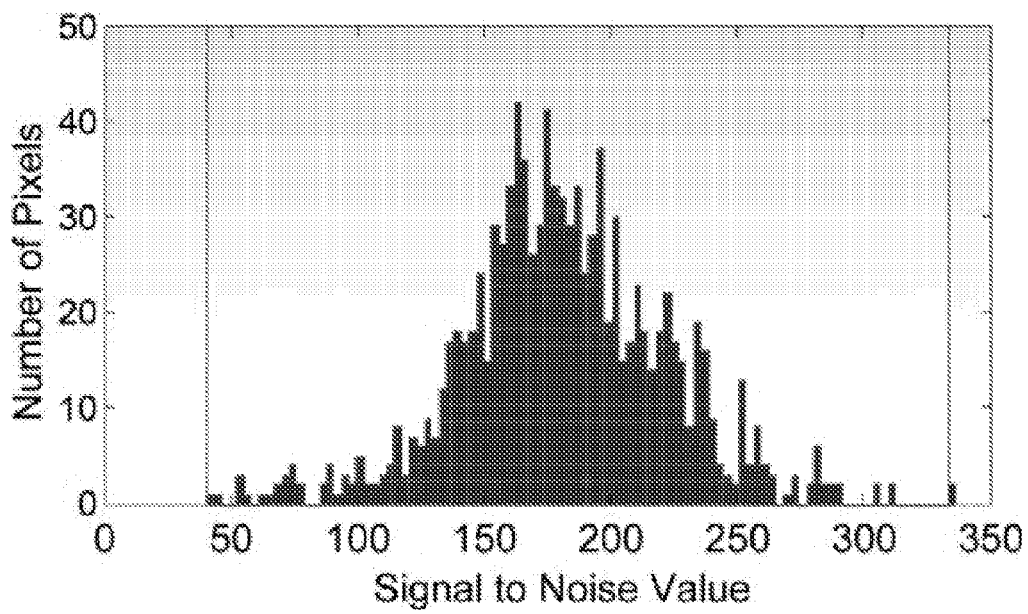
Figure 10:
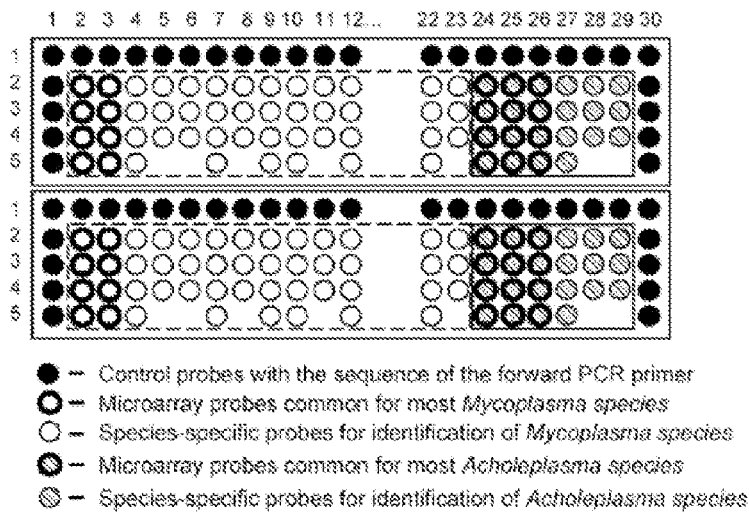

FIG. 7 illustrates one potential defect in microarray spots: a poorly shaped spot that consists mostly of a ring rather than a solid spot (in 3 dimensions, there is a concentric ring of peak intensity rather than a single peak). Such a defect probably originated during the printing of microarrays of oligonucleotide probes and may be related to probe concentration, spotting pin performance, or drying effects. This ring-shape has been found to occur when the volume of the suspension spotted by a pin on a slide was less than optimal during the robotic printing step.

Figure 8:
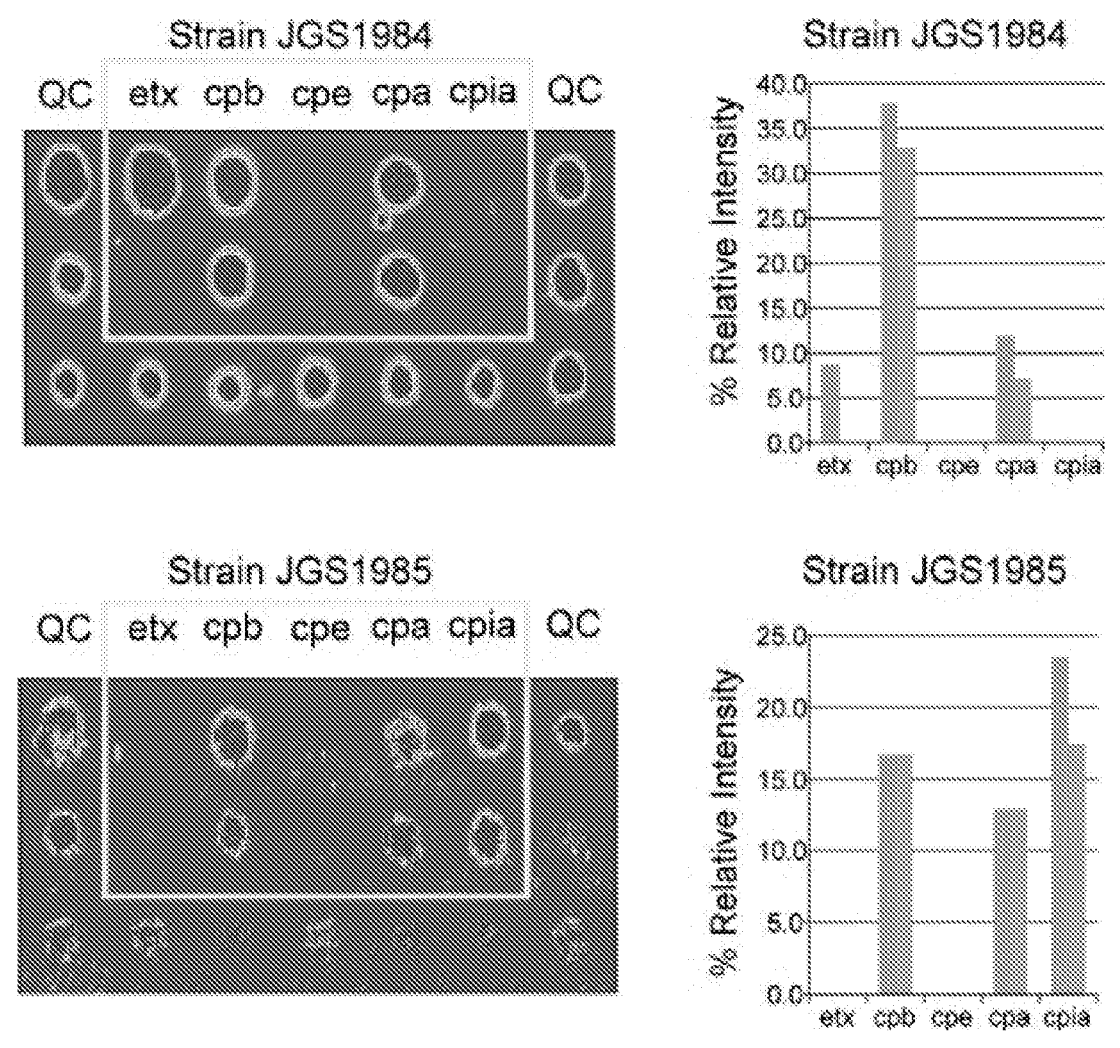

FIG. 8 presents a chemical image for each of two microarrays for detection of *C. perfringens* strains JGS1984 (upper row) and JGS1985 (bottom row) after hybridization with multiplex polymerase chain reaction products (targets). In each image, spots within the white rectangle contain probes for specific genes of the strains and spots outside the white rectangle are quality control (QC) spots.

The chemical images in FIG. 8 provide examples of satisfactory (JGS1984) and unsatisfactory (JGS1985) microarrays. In the image of the hybridized (JGS1985 microarray, all of the spots have unusually weak signals (FIG. 8) suggesting that the results may be unreliable. Such a defect might arise from analyst error such as excessive rinsing of the slide. Additionally, the QC spots on this microarray were poorly shaped or nearly missing, further suggesting unreliability of results from this microarray.

Another potential microarray defect is illustrated in FIG. 8 for the generally satisfactory JGS1984 microarray. One of the two replicate spots for the etx gene was unexpectedly missing from the microarray.

Thus, observation of hybridized spot morphology by ICRI can permit determination of defects in a nucleic acid microarray.

Example 9

Bacterial Identification

The identification of bacterial strains by nucleic acid microarrays can be based on qualitative determination of the presence or absence of specific genes of a given strain, for example the five *C. perfringens* genes, etx, cpb, cp, cpa and cpia. In particular, of these 5 genes, only etx, cpb and cpa are present in *C. perfringens* strain JGS1984.

FIG. 8 presents a chemical image and a histogram of relative intensity for two microarrays for detection of *C. perfringens* strains JGS1984 (upper row) and JGS1985 (bottom row) after hybridization with multiplex polymerase chain reaction products (targets) for the *C. perfringens* genes.

Strong hybridization of the three targets for etx, cpb and cpa to probe spots was observed only for the JGS1984 microarray. The presence of the three genes etx (only one spot), cpb, and cpa was used to correctly identify this strain. The corresponding relative intensities for the spots in each microarray are presented in the corresponding histogram in FIG. 8. In the histograms, the two bars shown for each gene represent the estimated relative intensities for each of the two duplicate spots in the corresponding microarray.

No strain identification was made from the results shown in FIG. 8 of hybridization with multiplex polymerase chain reaction products (targets) for the *C. perfringens* genes to the JGS1985 microarray. The ICRI results for this microarray were deemed unreliable, as discussed in the previous section.

For strain identification purposes, determination of relative intensity is sufficient. No absolute quantification of the intensity of each spot is necessary. In previous studies using fluorescence detection on similar arrays, a relative intensity of any spot in a given microarray greater than 2% of the total intensity for all the spots in the same microarray is deemed to represent a positive signal of hybridization at the spot; a spot with relative intensity below this threshold is deemed negative and cannot be used for identification or for confirming the presence of hybridization to the microarray.

Example 10

Estimation of Extent of Hybridization

Quantitative analysis of the spots in the images of FIG. 8 is carried out using ISys software. This determination for a given spot is based on measuring the integrated intensity over the spectral range between 1400 and 956 $cm^{-1}$ for the Si—O stretching vibration band, i.e., the most intense feature in the observed on-spot spectra (see FIG. 4). Over this spectral range, both diffuse and specular reflection modes occur (FIGS. 4, 5). Since spots are not uniformly circular and could suffer from drying effects, an arbitrary number of 100 pixels (spectra) in the middle of a spot is selected for such a measurement in order to exclude those pixels that are located at the boundary of a spot.

For the two microarrays shown in FIG. 8, which provide representative examples of intense as well as relatively weak spots, extent of hybridization is represented in plots displaying the intensity for a given spot in an array relative to the intensities of all the spots in the same array are shown.

In other analyses, the absolute value of the area under the band is used to determine intensity of the spot.

Example 11

Signal-to-Noise Ratio

A high signal to noise ratio (SNR) offers several potential benefits including improved reproducibility, accuracy, and throughput. The SNR was also estimated for these IR chemical images.

One method used to estimate SNR herein defines SNR as the ratio of the maximum intensity of the most intense band in a spectrum to the standard deviation in a limited spectral range where there is no band. The maximum intensity near 1180 $cm^{-1}$ was used as a measure of signal, and noise (16) was determined over the range of 1150-1000 $cm^{-1}$ in the absence of a hybridized spot. Typical SNR values were found in the range 16:1 to 35:1 for weak spots (as observed for strain JGS1985, FIG. 8); higher values were obtained (e.g., 230:1) for intense spots (strain JGS1984, FIG. 8).

A second SNR calculation method was performed using ISys software as outlined in its User's Manual. Using the ISys software, SNR estimates were obtained for the selected spectral range of 1150-1000 $cm^{-1}$ and for a spatial area defined by all 1024 pixels in an image for a non-hybridized spot. With this method, the lowest SNR values typically fell near 40:1 (see t example of a histogram of SNR for the pixels of a single image in FIG. 9).

The SNR values estimated for IRCI in this study are similar to those reported for fluorescent DNA microarrays, which range from approximately 50:1 to 200:1 in many applications. However, in some quantitative applications of fluorescent DNA microarray detection (e.g., gene expression profiling) with high-density chips, the SNR was reported to be as low as 2:1.

The spatial resolution capability of IRCI in the external reflection mode provided intrinsic image contrast, and permitted detection of DNA microarray hybridization on glass slides for the first time.

The silver enhancement protocol permitted the archiving of microarrays on glass slides.

Distinctive chemical images were used to discriminate between diffuse reflection and specular reflection.

The IRCI detection protocol of nucleic acid microarrays can be used in the identification of strains of various food-borne bacteria pathogens.

Example 12

Detection of *Mollicutes* Species Using IRCI Microarray-Based Detection

The *Mycoplasma* species, *M. bovis* (ATCC 25025), *M. primatum* (ATCC 25948), *M. pirum* (ATCC 25960), *M. synoviae* (ATCC 25204), *M. pneumoniae* (ATCC 15531), *A. laidlawii* (ATCC 23206), used in this study were obtained from the American Type Culture Collection (ATCC, Manassas, Va.). The growth of selected *Mollicutes* species was conducted using broth media and environmental conditions recommended by the suppliers. Mycoplasmal genomic DNA was isolated from the samples containing mycoplasma species using a method described in the art.

The universal PCR primers, 5'Biotin-GGTGAATACGTTCTCGGGTCTTGTACACAC (forward) (SEQ ID NO. 6) and TNCTTTTCACCTTCCCTCACGGTAC (reverse) (SEQ ID NO. 7), were used to amplify the 16-23S ITS region from all tested mycoplasmas. Single-stranded DNA (ssDNA) was prepared and hybridized to microarray using methods known in the art. The layout of this array is shown in FIG. 10. The *Mollicutes* microarrays were prepared by spotting the synthetic amine-modified species-specific oligonucleotide capture probes on aldehyde-coated glass microscope slides to produce a monolayer of single-stranded oligonucleotide probes that were immobilized via a covalent amide linkage (FIG. 2).

Spectral images were collected with an Agilent FTIR spectrometer model 7000e operating under Agilent FTIR Resolution Pro 4.0 software (Agilent FTIR, Melbourne, Australia) and equipped with a UMA 600 infrared microscope and a 32×32 (or 1024) pixels MCT focal-plane array detector. Each spectral image was obtained from approximately a 180×180 $\mu m^2$ test sample area with a nominal spatial resolution of 5.6 μm per pixel and a spectral resolution of 8 $cm^{-1}$. For each image, 16 co-added scans were collected and required approximately 16 sec of acquisition time.

The IRCI permitted the sensitive and efficient differentiation between hybridized and non-hybridized microarray spots. The most distinctive mid-infrared chemical images with maximum contrast were measured at 8 cm$^{-1}$ resolution at a discrete wavenumber, namely 1180 cm$^{-1}$ attributed to silicate glass Si—O stretching vibration, for all pixels over a hybridized DNA spot in an image. Images collected for microarray spots were measured relative to that of a background area on the slide located adjacent to a microarray. A bare portion of the glass slide was used for measuring reference background single beam spectra in order to maximize the qualitative (and quantitative, if required) differences between spectra observed for hybridized and non-hybridized microarray spots.

Figure 11:
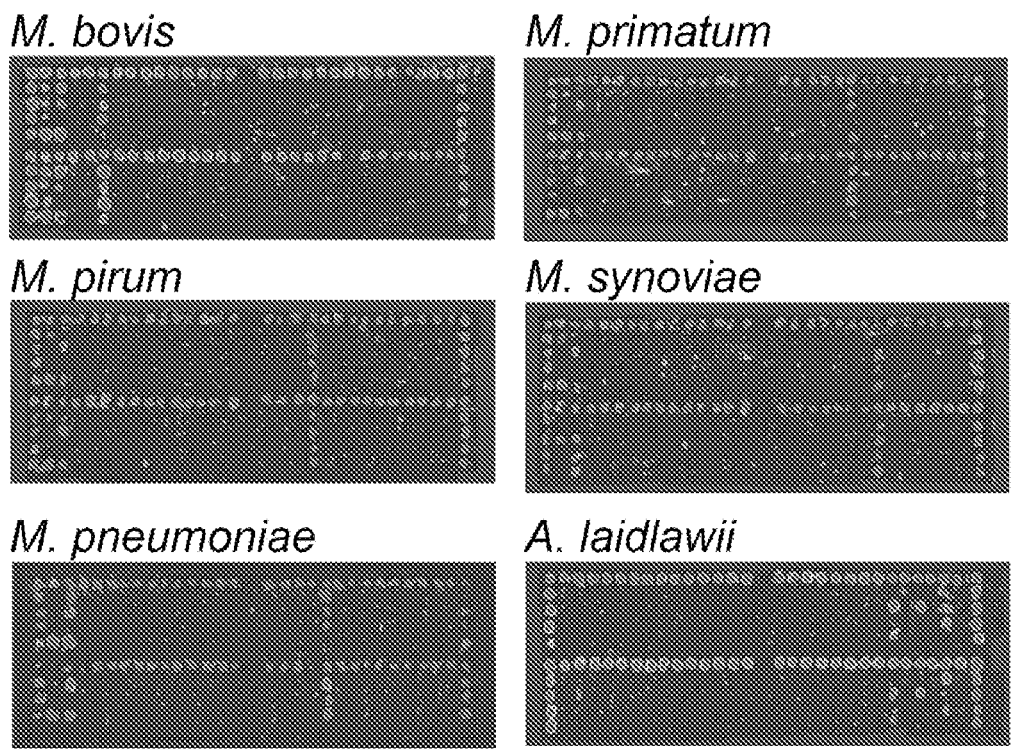
Figure 12:
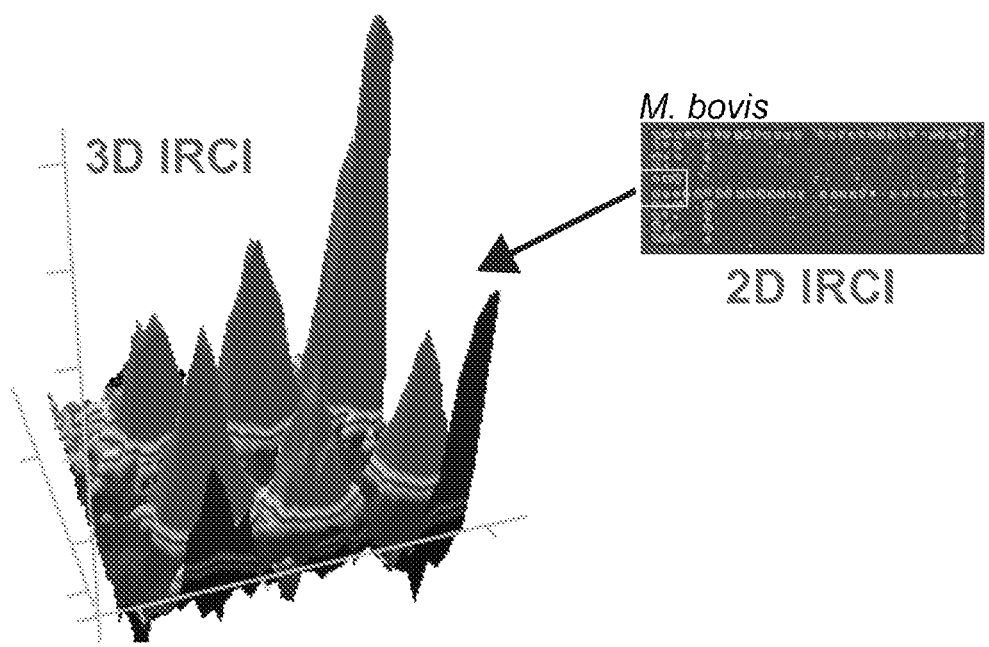

All species investigated were unambiguously identified by using IRCI detection in the present study. IRCI results consistent with the detection of DNA microarray and identification of *Mollicutes* species are shown in FIGS. 11 and 12. All the tested targets for the various species investigated exhibited specific hybridization with the microarray oligoprobes designed to specifically recognize individual *Mollicutes* species used in the study. Although some minor inter-species hybridization was detected, it did not affect the microarray-based *Mollicutes* species identification.

The sensitivity of the infrared imaging read-out method was also investigated. The determination of the lowest possible target concentration that corresponds to the limit of detection would be important for potential quantitative applications. The concentration of targets used in the present study was 50 nM, and was found to be adequate for the qualitative detection of microarrays. The signal-to-noise ratio (SNR) was 50:1 and consistent with those previously found. To evaluate the sensitivity of the infrared imaging methodology, reference synthetic target solutions with concentrations of 25 nM, 12.5 nM, 6.25 nM, 3.13 nM, and 1.5 nM were tested. A 22-mer nucleotide sequence that is used as a quality control, namely *Yersinia enterocolitica* virulence gene ail P3, was used for this quantitative evaluation. All the target concentrations used gave rise to microarrayed spots that were detectable by infrared imaging. At the lowest target concentration used (1.5 nM) the SNR was 4:1 and considered to be the lower limit of detection. It is noted that for studies where quantification is required, as in gene expression profiling, SNR values were reported in the literature for fluorescent DNA microarrays to be as low as 2:1. The microarray method in combination with IRCI were demonstrated to be a reliable tool for detection and identification of mycoplasmal agents in biological samples.

Example 13

Use of IRCI to Type *Y. Enterocolitica* Isolates

Strains: The *Y. enterocolitica* strains (FDA culture collection) used in this study are listed in Table 1. Brain Heart Infusion (BHI) medium was used to grow the 19 *Y. enterocolitica* strains. Bacterial DNA was isolated using a Gentra® Puregene DNA Isolation Kit (Qiagen, Valencia, Calif.).

Design of PCR primers and gene-specific oligonucleotide probes: ArrayDesigner software (Premier Biosoft International, Palo Alto, Calif.) was used to design individual gene-specific oligoprobes complimentary to unique sequences present within the target genes. The sequences of all oligonucleotide probes are shown in Table 2. The uniqueness of the designed oligoprobes was confirmed using a Blast Genbank search of homologous sequences. Both positive and negative controls were amplified with multiplex PCR and hybridized to the chip. A region of the 16S ribosomal DNA gene conserved among all Gram-negative species, including *Yersinia*, served as the positive control. An oligoprobe designed for the CPA gene of *Clostridium perfringens* was used as the negative control. An amino group was added to the 3' end of each oligonucleotide during synthesis to allow for covalent attachment to the glass slides pre-functionalized with succinimidyl ester groups (SurModics, Eden Prairie, Minn.). All DNA oligonucleotide probes and biotin-labeled forward primer oligonucleotides were synthesized by Integrated DNA Technologies (Coralville, Iowa). VirF, located on the pYV plasmid, has important regulatory functions. Although pYV is necessary for full virulence, other chromosomally encoded virulence factors are involved in *Y. enterocolitica* pathogenesis as well. The chromosomal ail gene encodes for a peptide that facilitates bacterial attachment and invasion to epithelial cells. Yst, encoded by the chromosomal yst gene, is an important heat-stable enterotoxin. The blaA gene encodes a β-lactamase which confers resistance to β-lactam antibiotics. β-lactamases are widely distributed in both clinical and environmental *Y. enterocolitica* strains.

TABLE 2

Oligonucleotide (probes) and PCR primers for *Y. enterocolitica* Isolates

| Target gene | GenBank accession no. | Frag. size (bp) | Tm (° C.) | Name | Primers (F1, R1) and oligonucleotide target sequence 5'-3' | SEQ ID NO: |
|---|---|---|---|---|---|---|
| VirF | AF102990 | 232 | 55 | F1 | GCTTTTGCTTGCCTTTAGCTCG | 8 |
|  |  |  | 55 | R1 | AGAATACGTCGCTCGCTTATCC | 9 |
|  |  |  | 54 | P1 | TTATTCCTCTCGGCTCTGCG | 10 |
|  |  |  | 53 | P2 | GCAACCGCCCAGAAGAAC | 11 |
|  |  |  | 61 | P5 | GGCATGGGATTAACCACATTCA | 12 |
| ail | AY004311 | 355 | 50 | F1 | TGGTTATGCACAAAGCCATGT | 13 |
|  |  |  | 52 | R1 | TGGAAGCGGGTTGAATTGCA | 14 |
|  |  |  | 59 | P3 | ACCTGAAGTACCGTTATGAACT | 15 |
|  |  |  | 61 | P4 | GCCATCTTTCCGCATTAACGA | 16 |
|  |  |  | 61 | P5 | TCGTTTGCTTATACCCATCAGG | 17 |
| yst | U09235 | 421 | 61 | F1 | TTGAAATAACTAGGCTGGGTCG | 18 |
|  |  |  | 61 | R1 | GCAACATACATCACAGCAATCC | 19 |
|  |  |  | 61 | P4 | AATAGAATGCGTGGTAGACCG | 20 |
|  |  |  | 61 | P5 | CTGTTATTGACACCACTGCGT | 21 |
|  |  |  | 59 | P8 | TGAGTGATGGAGGATCTATGAA | 22 |

TABLE 2-continued

Oligonucleotide (probes) and PCR primers
for Y. enterocolitica Isolates

| Target gene | GenBank accession no. | Frag. size (bp) | Tm (° C.) | Name | Primers (F1, R1) and oligonucleotide target sequence 5'-3' | SEQ ID NO: |
|---|---|---|---|---|---|---|
| blaA | X57074 | 478 | 54 | F1 | AAATGCGCTACCGGCTTCAG | 23 |
|  | S54099 |  | 54 | R1 | AGTGGTGGTATCACGTGGGT | 24 |
|  |  |  | 51 | P1 | TGCTGCCACCATTCAATATAGT | 25 |
|  |  |  | 60 | P3 | AAGCCAGTCTCAGCCGAAT | 26 |
|  |  |  | 61 | P4 | TCAGATGTTCAGATTAGACCGC | 27 |
| 16S | Z49829 | 382 | 62 | F1 | TCTGGGAAACTGCCTGATGG | 28 |
|  |  |  | 63 | R1 | GGTGCTTCTTCTGCGAGTAAC | 29 |
|  |  |  | 62 | P1 | ACACTGGAACTGAGACACGG | 30 |
|  |  |  | 62 | P2 | CAGCGAGGAGGAAGGCATAA | 31 |
|  |  |  | 63 | P3 | CTAGCTGGTCTGAGAGGATGA | 32 |

Microarray printing: Microarrays were printed as in Example 2. The layout of arrays is shown in FIG. 13.

Printed glass slides were incubated overnight at room temperature in a storage chamber partially filled with a saturated solution of NaCl. The prefunctionalized surface of the slides was blocked for 30 min using 50 mM ethanolamine blocking solution pre-warmed to 50° C. The slides were then rinsed with deionized water and washed with 4×SSC, 0.1% sodium dodecyl sulfate (SDS) (pre-warmed to 50° C.). Finally, the slides were rinsed again with deionized water followed by drying using centrifugation at 800 rpm for 3 min.

Single polymerase chain reaction (PCR) amplification of five Y. enterocolitica genes: The PCR mixture (50 µl) contained 14 pmol of each primer, approximately 1 µg of DNA template, 4 mM MgCl$_2$, and 25 µl of HotStarTaq™ DNA Master Mix (Qiagen, Inc., Valencia, Calif.). The following conditions were used for PCR amplification: initial enzyme activation at 95° C. for 5 min, 35 cycles at 94° C. for 25 s, 50° C. for 25 s and 72° C. for 30 s, and final elongation at 72° C. for 5 min. Molecular weights of the PCR products were confirmed with gel electrophoresis using a 2% agarose gel.

Multiplex PCR amplification: The multiplex PCR reaction (50 µl) was conducted using conditions similar to that described above for the single PCR reaction except for the use of lower amount of DNA template (approximately 500 ng instead of 1 µg).

Preparation of biotinylated ssDNA targets for microarray hybridization and infrared imaging of microarrays and ATR-FTIR data acquisition were done as in Example 3 except an Agilent FTIR spectrometer model 7000e operating under Agilent FTIR. Resolution Pro 5.1 software (Agilent FTIR, Melbourne, Australia) was used. Spot intensity was obtained from the observed infrared interferograms at a given pixel by averaging the maximum intensity values for five of the most intense pixels in an image of an individual spot. All measurements were carried out in triplicate on microarrays printed and hybridized on three different days.

Multiplex PCR gel electrophoresis for each of the four virulence genes (virF, ail, yst, and blaA) and the 16S ribosomal DNA gene was used to detect the presence or absence of each gene in individual Y. enterocolitica strains. Results of multiplex PCR amplification analysis are shown in Table 3. All 19 Y. enterocolitica strains investigated showed the efficient amplification of conserved region of 16S rRNA gene used as a positive control for the PCR reaction. Nine Y. enterocolitica isolates (231, 229, 227, 225, 222, 197, 97, 52, 53) did not have any of the four virulence genes. The presence of the virF gene was found in Y. enterocolitica strains 133, 88, and 37. Only three isolates (88, 14, 35) had the blaA gene. The ail and yst virulence genes were detected in the following strains: 188, 133, 164, 103, 60, 88, 38, 37, 14 and 35.

TABLE 3

Y. enterocolitica isotyping by using microarray chips with IRCI detection and by PCR

| Y. enterocolitica | VirF | | Ail | | Yst | | BlaA | | Non-specific 16S | |
|---|---|---|---|---|---|---|---|---|---|---|
|  | PCR | Chip | PCR | Chip | PCR | Chip | PCR | Chip | PCR | Chip |
| 231 | − | − | − | − | − | − | − | − | + | + |
| 229 | − | − | − | − | − | − | − | − | + | + |
| 227 | − | − | − | − | − | − | − | − | + | + |
| 225 | − | − | − | − | − | − | − | − | + | + |
| 222 | − | − | − | − | − | − | − | − | + | + |
| 197 | − | − | − | − | − | − | − | − | + | + |
| 188 | − | − | + | + | + | + | − | − | + | + |
| 133 | + | + | + | + | + | + | − | − | + | + |
| 164 | − | − | + | + | + | + | − | − | + | + |
| 97 | − | − | − | − | − | − | − | − | + | + |
| 103 | − | − | + | + | + | + | − | − | + | + |
| 60 |  |  | + | + | + | + | − | − | + | + |
| 88 | + | + | + | + | + | + | + | + | + | + |
| 52 | − | − | − | − | − | − | − | − | + | + |
| 53 | − | − | − | − | − | − | − | − | + | + |
| 38 | − | − | + | + | + | + | − | − | + | + |
| 37 | + | + | + | + | + | + | − | − | + | + |

TABLE 3-continued

Y. enterocolitica isotyping by using microarray chips with IRCI detection and by PCR

| Y. enterocolitica | VirF | | Ail | | Yst | | BlaA | | Non-specific 16S | |
|---|---|---|---|---|---|---|---|---|---|---|
| | PCR | Chip | PCR | Chip | PCR | Chip | PCR | Chip | PCR | Chip |
| 14 | − | − | + | + | + | + | + | + | + | + |
| 35 | − | − | + | + | + | + | + | + | + | + |

Each spot in a microarray observed by IR imaging in the reflection mode appeared as a highly intense 3-D column with high contrast over a horizontal background (See e.g., FIG. 14, exemplified for the ail gene). IRCI microarray data were consistent with those obtained by PCR (Table 3). Genes that were present in each Yersinia strain had positive signals whereas genes that were absent had no signal. All Y. enterocolitica strains appeared to have a positive chip hybridization signal for the 16S ribosomal DNA genes. As expected, no signal was found for CPA. The IRCI signal intensity observed for the various strains were satisfactorily used to identify virulence genes. For the 19 Y. enterocolitica strains investigated, quantitative histograms of the percent relative infrared imaging intensities (y-axis) for the four virulence genes (virF, ail, yst, and blaA), the 16S positive control gene, and the CPA gene negative control were determined (data not shown). An exemplary histogram for Strain 231 is shown in FIG. 15. Three replicate IRCI measurements for each gene were obtained on three different days and averaged. The standard deviation for each of the gene segments was calculated, and the relative intensity values for each gene segment were within two standard deviations of the mean. No cross-hybridization was observed.

We successfully determined the presence or absence of four Y. enterocolitica virulence genes in 19 strains by using a DNA microarray fluorophore-free protocol that is based on the silver enhancement of gold nanoparticles and the novel infrared imaging read-out method in the reflection mode.

It may be helpful in the understanding of the present disclosure to set forth definitions of certain terms used herein.

The terms "a" and "an" do not denote a limitation of quantity, but rather denote the presence of at least one of the referenced items. The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and the all ranges, including endpoints, are independently combinable. The modifier "about" used in connection with a quantity is inclusive of the stated value and has the meaning dictated by the context (e.g., includes the degree of error associated with measurement of the particular quantity).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

All references are incorporated by reference herein in their entirety.

Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

The invention claimed is:

1. A method for detecting presence or absence of a target in a sample, the method comprising:
   contacting a nucleic acid capture probe attached to an addressable location on a solid infrared absorbing surface with the sample under conditions effective to form a hybridization complex between the nucleic acid capture probe and the target;
   conjugating the hybridization complex to a nanoparticle to form a conjugated hybridization complex;
   binding silver to the conjugated hybridization complex to provide silver enhancement of the conjugated hybridization complex;
   exposing the solid infrared absorbing surface containing the conjugated hybridization complex to light having a wavenumber of 1400 cm$^{-1}$ to 956 cm$^{-1}$; and
   determining, in external reflection mode, any reflectance from the solid infrared absorbing surface, wherein measurable mid-infrared reflectance indicates the presence of the target in the sample.

2. The method of claim 1, wherein the nanoparticle is a gold nanoparticle.

3. The method of claim 1, wherein the target is biotinylated and is then conjugated with a streptavidin-nanoparticle.

4. The method of claim 1, wherein the nanoparticle is a gold nanoparticle.

5. The method of claim 1, wherein reflectance is detected with a mercury cadmium telluride focal plane array infrared detector.

6. The method of claim 1, further comprising quantification of the amount of target that is hybridized by integrating the intensity over a selected spatial range defined by pixels over a hybridized spot.

7. The method of claim 1, wherein the capture probe attached to the infrared absorbing surface is in the form of a microarray.

8. The method of claim 1, wherein the capture probe is a gene-specific oligoprobe complimentary to a unique sequence present within a target gene of a pathogenic organism.

9. The method of claim 8, wherein the pathogenic organism is a pathogen found in contaminated food.

10. The method of claim 8, wherein the pathogenic organism found is a *Mycoplasma* species or a *Yersinia* species.

11. The method of claim 1, wherein determining comprises focal plane array Fourier transform mid-infrared (FTIR) microspectroscopy to provide a three-dimensional image of the solid surface and a mid-infrared spectrum at each pixel of the image of the solid surface.

12. The method of claim 1, wherein determining, in external reflection mode, any reflectance from the solid surface with the contacted capture probes comprises determining both diffuse and specular reflection.

13. A method for identifying a defect in a nucleic acid microarray formed on a glass substrate,
contacting the nucleic acid microarray on the glass substrate with a solution comprising a nucleic acid target to hybridize with each spot of the microarray under conditions effective to form hybridization complexes between the targets and the spots on the microarray, wherein each spot on the microarray comprises a nucleic acid capture probe;
conjugating the hybridization complexes to nanoparticles to form conjugated hybridization complexes;
binding silver to the conjugated hybridization complexes to provide silver enhancement of the hybridization complexes;
imaging the hybridized microarray with mid-infrared radiation in the external reflection mode to produce an image, wherein the mid-infrared radiation has a wavenumber of 1400 $cm^{-1}$ to 956 $cm^{-1}$; and
identifying a defect in the microarrays from the spot morphology or relative reflectance intensity in the image.

14. The method of claim 13, wherein imaging the hybridized microarray with mid-infrared radiation comprises determining, in external reflection mode, both diffuse and specular reflection.

15. A method for comparing relative quantities of a nucleic acid target in two or more samples, the method comprising:
contacting a nucleic acid capture probe attached to an addressable location on a solid infrared absorbing surface with a sample to be analyzed for the nucleic acid target under conditions effective to form a hybridization complex between the nucleic acid capture probe and the nucleic acid target;
conjugating the hybridization complex to a nanoparticle to form a conjugated hybridization complex
binding silver metal to the conjugated hybridization complex to provide silver enhancement of the conjugated hybridization complex;
imaging the solid infrared absorbing surface with mid-infrared radiation in the external reflection mode to produce an image and to determine relative intensity of the image for the target for the sample, wherein the mid-infrared radiation has a wavenumber of 1400 $cm^{-1}$ to 956 $cm^{-1}$;
repeating the contacting and imaging steps for the target in a second sample; and
comparing the relative intensities of the images for the target in the two samples to determine the relative quantities of the target in the two samples.

16. The method of claim 15, wherein imaging the solid infrared absorbing surface with mid-infrared radiation comprises determining, in external reflection mode, both diffuse and specular reflection.

* * * * *